(12) United States Patent
He et al.

(10) Patent No.: US 9,096,678 B2
(45) Date of Patent: Aug. 4, 2015

(54) RICE BROWN PLANTHOPPER RESISTANCE GENE AND APPLICATIONS THEREOF

(75) Inventors: Guangcun He, Wuhan (CN); Bo Du, Wuhan (CN); Weilin Zhang, Wuhan (CN); Lili Zhu, Wuhan (CN); Rongzhi Chen, Wuhan (CN)

(73) Assignee: WUHAN UNIVERSITY, Hubei (CN)

( * ) Notice: Subject to any disclaimer, the term of this patent is extended or adjusted under 35 U.S.C. 154(b) by 1063 days.

(21) Appl. No.: 13/143,383

(22) PCT Filed: Dec. 30, 2009

(86) PCT No.: PCT/IB2009/007988
§ 371 (c)(1), (2), (4) Date: Aug. 12, 2011

(87) PCT Pub. No.: WO2010/079383
PCT Pub. Date: Jul. 15, 2010

(65) Prior Publication Data
US 2011/0289619 A1  Nov. 24, 2011

(30) Foreign Application Priority Data
Jan. 6, 2009   (CN) .......................... 2009 1 0076514

(51) Int. Cl.
C07K 14/415 (2006.01)
A01H 1/04 (2006.01)
A01H 5/10 (2006.01)
C12N 15/82 (2006.01)

(52) U.S. Cl.
CPC ................ *C07K 14/415* (2013.01); *A01H 1/04* (2013.01); *A01H 5/10* (2013.01); *C12N 15/8286* (2013.01)

(58) Field of Classification Search
None
See application file for complete search history.

(56) References Cited

FOREIGN PATENT DOCUMENTS

| CN | 101463354 A | 6/2009 |
|---|---|---|
| WO | WO2010079383 A3 | 7/2010 |

OTHER PUBLICATIONS

Hao et al. (Plant Physiology, Apr. 2008, vol. 146, pp. 1810-1820).*
Du et al. (PNAS, Dec. 29, 2009, vol. 106, No. 52, pp. 22163-22186).*
GenBank accession No. FJ941067.*
Du, B. et al., Identification and characterization of Bph14, a gene conferring resistance to brown planthopper in rice. PNAS, Dec. 29, 2009, vol. 106, No. 52, 22163-22168.
Hao, P. et al., Herbivore-Induced Callose Deposition on the Sieve Plates of Rice: An Important Mechanism for Host Resistance. Plant Physiology, Apr. 2008, vol. 146, pp. 1810-1820.
Huang, Z. et al., Identification and mapping of two brown planthopper resistance genes in rice. Theor Appl Genet, 2001, 102:929-934.
Jairin, J. et al., Detection of Brown Planthopper Resistance Genes from Different Rice Mapping Populations in the Same Genomic Location. ScienceAsia 33, 2007, pp. 347-352.
He, GC., Applied Plant Genomics: From Genome to Field, Brown Planthopper Resistence Genes in Rice: from Germplasm to Breeding. Molecular Plant breeding, 2007, vol. 5, No. 2, 175-176.
Ren, X. et al., Dynamic mapping of quantitative trait loci for brown planthopper resistance in rice. Wuhan University, College of Life Sciences. Cereal Research Communications. 2004, vol. 32, No. 1, pp. 31-38.
Ren, X. et al., Mapping quantitive trait loci and expressed sequence tags related to brown palnthopper resistance in rice. Plant Breeding, 2004, 123, 342-348 (ISSN 0179-9541).
Sun L. et al., Identification of quantitative trait loci associated with resistance to brown planthopper in the indica rice cultivar Col. 5 Thailand. Hereditas, 2007, 144: 48-52, Lund, Sweden.
Tan, GX et al., Two whitebacked planthopper resistance genes in rice share the same loci with those for brown planthopper resistance. Heredity, 2004, 92, 212-217, Nature Publishing Group.
Wang, Y. et al., Responses of Two Contrasting Genotypes of Rice to Brown Planthopper. Molecular Plant-Microbe Interactions, 2008, vol. 21, No. 1, pp. 122-132, The American Phytopathological Society.
Yang, H. et al., High-resolution genetic mapping at the Bph15 locus for brown planthopper resistance in rice (*Oryza sativa* L.). Theor Appl Genet, 2004, 110: 182-191.
Zhang, Qifa, Strategies for developing Green Super Rice. PNAS, Oct. 16, 2007, vol. 104, No. 42, pp. 16402-16409.
Li, R., et al., Identification and genetics of resistance against brown planthopper in a derivative of wild rice, *Oryza rufipogon* Griff. J. Genet. & breed. 56:29-36 (2002).
Li, Jinbo et al. Marker-assisted selection for brown planthopper (*Nilaparvata lugens* Stal) resistence genes Bph14 and Bph15 in rice. Scientia Agricultura Sinica, Oct. 30, 2006, vol. 39, No. 10, pp. 2132-2137, ISSN 0578-1752.
Brar, D., et al., Breeding for resistance to planthoppers in rice. Rice Planthopper Project, 2009, pp. 401-127 (International Rice Research Institute); ISBN978-971-22-0251-3.

\* cited by examiner

*Primary Examiner* — David T Fox
*Assistant Examiner* — Jared Shapiro
(74) *Attorney, Agent, or Firm* — John P. White; Cooper & Dunham LLP

(57) ABSTRACT

The present invention provides rice brown planthopper resistance gene Bph14. It has a nucleotide sequence as shown in SEQ ID NO:1 and its cDNA sequence is shown in SEQ ID NO:2. The Bph14 gene in the present invention belongs to the CC-NBS-LRR gene family, its coded protein is related to plant disease resistance. Bph14 gene has the function of resisting brown planthopper. By introducing Bph14 gene into ordinary rice variety through genetic transformation and cross breeding, the brown planthopper resistance of rice can be increased, so that the harm caused by brown planthopper can be alleviated and the aim of increasing and stabilizing production can be achieved.

6 Claims, 2 Drawing Sheets

RICE BROWN PLANTHOPPER RESISTANCE GENE AND APPLICATIONS THEREOF

FIELD OF THE INVENTION

The present invention belongs to the field of plant gene engineering. Specifically, it relates to a rice brown planthopper resistance gene Bph14 and the use of the gene in rice and rice seed to resist brown planthopper.

BACKGROUND

Rice is a very important food crop, which serves as staple food for more than half of the world's population. Furthermore, detailed genetic mapping and physical mapping of the rice genome is complete. Creating transgenic rice has become routine. Additionally, rice has colinearity with the genomes of other gramineous crops, therefore it has been viewed as a model plant. Therefore, the study of rice functional genes has significant meanings for social economic development and biological research.

The lack of adequate food supply is a challenge faced by the entire world. Rice yield has been dramatically increased by the two technology revolutions of dwarf rice plant of the 1950s and 1960s, and the hybrid rice of the 1970s. However, rice crops are still harmed by pests over large areas and rice production remains threatened, particularly by brown planthopper. Brown planthopper adults and nympha stab and suck the rice sap with their stylets, causing the leaves to turn yellow or to wither to death, which results in reduction or total destruction of the yield. According to China agriculture yearbook, there were severe outbreaks of brown planthopper nation wide in the years 1966, 1969, 1973, 1977, 1983 and 2003 and extremely severe outbreaks in the years 1987, 1991, 2005, 2006 and 2007. The harmed area accounts for more than 50% of the total rice cultivation and it caused a great loss to the rice production of China. Since the harm caused by brown planthopper occurs mainly during rice grain filling and ripening stages, large amounts of pesticide must be applied during this period, which risks contaminating the rice. There remains a need in the industry for a safer way to ensure a high yield from rice cultivation.

Using a brown planthopper resistance gene to breed pest resistance into a rice variety is the most economic and effective method for the integrated control of brown planthopper. The research results of International Rice Research Institute (IRRI) and the practical experience of rice production in Southeast Asia have shown that even rice varieties having medium level resistance are sufficient to control the brown planthopper population so as to have no discernable damage and that no actual harm and loss of yield are caused. Thus, isolating a brown planthopper resistance gene and applying it in the project of rice breeding are the fundamental measures for controlling damage in rice crops caused by brown planthopper.

The study of rice brown planthopper resistance gene began in the 1970s. Up to now, 19 major pest resistance genes have been named (for detailed reviews see Yang H Y et al., 2004 High-resolution genetic mapping at the Bph15 locus for brown planthopper resistance in rice. *Theor Appl Genet.* 110: 182-191). Among them, the resistance of the three rice varieties (Mudgo, CO22 and MTU15) is controlled by a single dominant gene, this gene is named as Bph1, and another recessive gene bph2, closely linked with Bph1, controls the resistance of rice variety ASD7. In their genetic study of 28 varieties, Lakshminarayana and Khush found that rice variety Rathu Heenati carries a dominant brown planthopper resistance gene Bph3, which is inherited independently from BPh1. In addition, rice variety Babawee contains a recessive gene bph4, which is also inherited independently from bph2. Sidhu and Khush found that Bph3 and bph4 are closely linked, bph4 is also linked with the semidwarf gene sd-1. The genetic analysis of Khush et al about rice variety ARC10550 showed that it contains the recessive gene bph5. In their study of 17 materials resistant to bio-type 4 BPH but sensitive to the other three bio-types, Kabir and Khush found that varieties Swarnalata and T12 contain one pest resistance gene respectively, which are named Bph6 and bph7. The discovery of bph8 and Bph9 is similar to that of the other genes, the recessive gene bph8 is not allelic to bph2 and bph4, the dominant gene. Bph9 is not allelic to Bph3 and Bph4. Among the afore-mentioned brown planthopper resistance genes, bph5, Bph6 and bph7 are resistant to brown planthopper bio-type 4, while exhibiting sensitivity to bio-types 1, 2 and 3.

Wild rice is also a source of brown planthopper resistance genes. In 1994, Ishii et al. identified a new dominant brown planthopper resistance gene Bph10 from a transformed line of Australian wild rice (*O. australiensis*), IR65482-4-136-2-2. This gene is resistant to brown planthopper bio-types 1, 2 and 3. Bph11 is identified from *O. eichinger*. Rice with a brown planthopper resistance gene can inhibit food fetching, growth and development, and reproduction of brown planthopper, so that the aim of pest resistance is achieved (Hao PY et al., 2008 Herbivore-induced callose deposition on the sieve plates of rice: an important mechanism for host resistance. *Plant Physiology* 146: 1810-1820). However, up to now, no rice brown planthopper resistance gene has been cloned.

Map-based cloning is also called positional cloning, which is a gene cloning technology developed along with the development of molecular marker genetic linkage map. The steps of map-based cloning comprise genetic mapping of the target gene, physical mapping, sequence analysis and genetic transformation and test of function. Theoretically, any gene that is able to be positioned can be isolated by map-based cloning. Generally, map-based cloning is suitable for species with relatively small genomes, such as the monocot model plant rice, in which the ratio between genome physical distance and genetic distance is small and has plenty of markers. As a gramineous model plant, rice has a genome that is the center of a concentric circle formed by the genomes of 7 gramineous plants, such as wheat and broomcorn, and it is one of the crops most suitable to use map-based cloning to isolate a target gene. Multiple genes already cloned in rice were cloned by map-based cloning, for example, the *Xanthomonas oryzae* pv. *oryzae* resistance gene Xa-21 (Song W Y et al. 1995, A Receptor Kinase-Like Protein Encoded by the Rice Disease Resistance Gene, Xa21. *Science,* 270: 1804-1806), Xa-1 (Yoshimura et al. 1998, Expression of Xa-1, a bacterial blight-resistance gene in rice, is induced by bacterial inoculation. *PNAS,* 95: 1663-1668) and Xa-26 (Sun et al. 2004, Xa26 a gene conferring resistance to *Xanthomonas oryzae* pv. *oryzae* in rice, encodes an leucine-rich repeat LRR receptor kinase-like protein. *Plant Journal,* 37: 517-527), rice blast resistance gene Pi-b (Wang et al. 1999, The Pi-b gene for rice blast resistance belongs to the nucleotide binding and leucine-rich repeat class of plant disease resistance genes. *Plant Journal,* 1999, 19: 55-64) and Pi-ta (Bryan et al. 2000, A single amino acid difference distinguishes resistant and susceptible alleles of the rice blast resistance gene Pi-ta. *Plant Cell,* 12: 2033-2046), and the tillering gene cloned by Li (Li et al. 2003, Control of tillering in rice. *Nature* 422: 618-621), salt tolerance gene (Ren et al. 2005, A rice quantitative trait locus for salt tolerance encodes a sodium transporter. *Nature Genetics* 37(10): 1141-1146) and high yield gene (Weiya Xue et al. 2008. Natural variation in Ghd7 is an important regulator of heading date and yield potential in rice. Nature Genetics 40, 761-767).

SUMMARY

The aim of the present invention is to provide a rice brown planthopper resistance gene Bph14, which has a nucleotide sequence as shown in SEQ ID NO:1.

Another aim of the present invention is to provide methods of using the brown planthopper resistance gene Bph14 to improve rice breeding.

A further aim of the present invention is to provide methods of using the brown planthopper resistance gene Bph14 to increase the resistance of rice to brown planthopper.

The present invention provides a method of establishing an isolated population of rice resistant to brown planthopper. It uses map-based cloning and isolates rice brown planthopper resistance gene Bph14. Co-segregation marker assay shows that this gene is co-separated with brown planthopper resistance property. By genetic transformation of the Bph14 gene, so that the transformed rice shows the phenotype of brown planthopper resistance, the function of this gene is proved.

The nucleotide sequence of the Bph14 gene of the present invention is as shown in SEQ ID NO:1. The full length of this gene is 9921 bp, containing 1 intron and 2 exons, its CDS are the regions base pairs 3387-7289 and base pairs 7936-8004 respectively. The full length of the cDNA is 3972 bp, encoding for 1323 amino acids, its amino acid sequence is as shown in SEQ ID NO:3. This protein belongs to the family of nucleotide-binding site—leucine-rich repeat NBS-LRR, the active center region of 180-464 is a conservative NB-ARC domain, including conservative P-loop, ATP binding domain and kinase 1a (Van der Biezen E A, Jones J D G. The NB-ARC domain: a novel signalling motif shared by plant resistance gene products and regulators of cell death in animals. 26 Mar. 1998. Current Biology 8(7):R226-R228).

It should be understood, without influencing the activity of the Bph 14 protein, the skilled person in the art can substitute, insert and/or delete one or more amino acids of the amino acid sequence as shown in SEQ ID NO:3 to make an amino acid sequence having the same function.

Besides, considering the degeneracy of codons, for example, the gene sequence coding for the above-mentioned protein can be modified in its coding region without changing the amino acid sequence or in the non-coding region without affecting protein expression. Therefore, the present invention also includes a nucleotide sequence with one or more nucleotide substituted, inserted and/or deleted from the gene sequence coding for the above protein and having the same function as the above coding gene. The present invention also comprises sense sequence or antisense sequence derived from the gene, including cloning vector or expression vector containing the nucleotide sequence or its fragment, host cell containing the vector, a transformed plant cell and a transgenic plant containing the nucleotide sequence or a fragment thereof.

The skilled person in the art will understand that molecular markers designed or made according to the published sequence of the present invention can be used for the breeding of brown planthopper resistant rice.

The advantage and effect of the present invention:
1. The successful cloning of the Bph14 gene further proved the ability of map-based cloning in cloning important rice genes. Genes cloned using this method have clear functions and beneficial effects.
2. Although in rice, multiple genes coding for nucleotide-binding site NBS structure containing proteins have been cloned, most of them are related to disease resistance. The Bph14 gene cloned in the present invention has the evident property of brown planthopper resistance and this is of great importance for fully understanding the biological functions for genes of this type.
3. To date, no rice brown planthopper resistance gene is known to have been cloned, and the molecular mechanism of resisting brown planthopper in rice remains unclear. The Bph14 gene cloned in the present invention can increase the resistance of rice against brown planthopper, which will promote research to understand the molecular mechanisms of brown planthopper resistance in rice.
4. Bph14 dramatically increases the brown planthopper resistance of rice. Using Bph14 for rice breeding via genetic transformation or cross-breeding can improve the resistance of rice against brown planthopper, so that the harm caused by brown planthopper is alleviated and the aim of increasing and stabilizing the yield is achieved.
5. The piercing-sucking insect is a detrimental pest to the agricultural industry. The cloning of the Bph14 gene and the verification of its brown planthopper resistance function serve as an important reference for studying resistance in other plants to other classes of piercing-sucking insects.

By using primers provided (SEQ ID NOs: 14-27), brown planthopper resistance may be determined. The existence of brown planthopper resistance gene Bph14 in rice variety B5 is indicated if 222 base pair (bp) fragments (SG1) can be amplified using SEQ ID NOs: 14 and 15; or 221 bp fragments (SG6) can be amplified using SEQ ID NOs: 16 and 17; or 227 bp fragments (SG9) can be amplified using SEQ ID NOs: 18 and 19; or 158 bp fragments (RM570) can be amplified using SEQ ID NOs: 20 and 21, or 230 bp fragments (SM1) can be amplified using SEQ ID NOs: 22 and 23; or 172 bp fragments (76-2) can be amplified using SEQ ID NOs: 24 and 25; or 218 bp fragments (SM4) can be amplified using SEQ ID NOs: 26 and 27; wherein the Bph14 gene locates between marker SG1 and SM4 in the end of the long arm of the $3^{rd}$ chromosome in rice genome. We have used SG1 and SM4 to screen 3700 single plants from the $F_2$ population and 5000 single plants from the $F_5$ population, and have acquired single plants that have recombinant molecular markers between SG1 and SM4. Based on the genotype of these recombinant single plants and the resistance grade of their corresponding lines, molecular marker 76-2 cosegregates with brown planthopper resistance gene Bph14, and molecular marker SG1, SG9, SG6, RM570, SM1 and SM4 all can be used to screen brown planthopper resistant rice varieties carrying Bph14 gene.

One aspect of the present invention provides an isolated nucleic acid molecule comprising a nucleotide sequence that comprises a brown planthopper resistance gene Bph14 selected from the group consisting of SEQ ID NO: 1 and SEQ ID NO: 2. In another aspect, the nucleotide sequence encodes a polypeptide molecule comprising the amino acid sequence SEQ ID NO: 3. In yet another aspect, the nucleotide sequence is operably linked to a heterologous promoter.

Another aspect of the present invention provides an expression vector comprising the isolated nucleic acid molecule comprising a nucleotide sequence that comprises a brown planthopper resistance gene Bph14 selected from the group consisting of SEQ ID NO: 1 and SEQ ID NO: 2. In yet another aspect, the present invention provides a transgenic plant, plant tissue, or plant cell comprising the expression vector. In still yet another aspect, the transgenic plant, plant tissue, or plant cell is a monocot. In further yet another aspect, the transgenic plant, plant tissue, or plant cell is rice.

Yet another aspect of the present invention provides a method for producing a transgenic plant which expresses a Bph14 gene, comprising the steps of: (a) stably transforming a cell of a plant with a nucleic acid molecule comprising a nucleic acid sequence selected from the group consisting of SEQ ID NO: 1 and SEQ ID NO: 2 to produce a transformed cell; (b) regenerating a transgenic plant from the transformed cell; and (c) growing the transgenic plant wherein the nucleic acid molecule is expressed. In another aspect, the transgenic plant is a monocot. In still yet another aspect, the transgenic plant is rice.

Further yet another aspect of the present invention provides a molecular marker associated with brown planthopper resistance, wherein the molecular marker is selected from the group consisting of: SG1, SG6, SG9, RM570, SM1, 76-2, and SM4. In one aspect, SG1 is amplified by primers SEQ ID NOs: 14 and 15. In another aspect, SG6 is amplified by primers SEQ ID NOs: 16 and 17. In yet another aspect, SG9 is amplified by primers SEQ ID NOs: 18 and 19. In still yet another aspect, RM570 is amplified by primers SEQ ID NOs: 20 and 21. In further yet another aspect, SM1 is amplified by primers SEQ ID NOs: 22 and 23. In another aspect, 76-2 is amplified by primers SEQ ID NOs: 24 and 25. In yet another aspect, SM4 is amplified by primers SEQ ID NOs: 26 and 27.

Still yet another aspect of the present invention is a method for determining the presence or absence of brown planthopper resistance in a plant or seed, comprising analyzing genomic DNA from the plant or seed for the presence of a molecular marker linked to a quantitative trait locus associated brown planthopper resistance, wherein the molecular marker is selected from the group consisting of SG1, SG6, SG9, RM570, SM1, 76-2, and SM4. In another aspect, the method further comprises analyzing genomic DNA from a plant or seed for the presence of a second molecular marker linked to a quantitative trait locus associated with brown planthopper resistance, wherein the second molecular marker is G1318. In yet another aspect, the plant or seed is a monocot. In still yet another aspect, the plant or seed is rice.

Another aspect of the present invention is a quantitative trait locus associated with brown planthopper resistance, wherein the quantitative trait locus is located in a 34 kb region between a first molecular marker and a second molecular marker on chromosome 3 of rice. In another aspect, the quantitative trait locus comprises Bph14.

Figure 1:
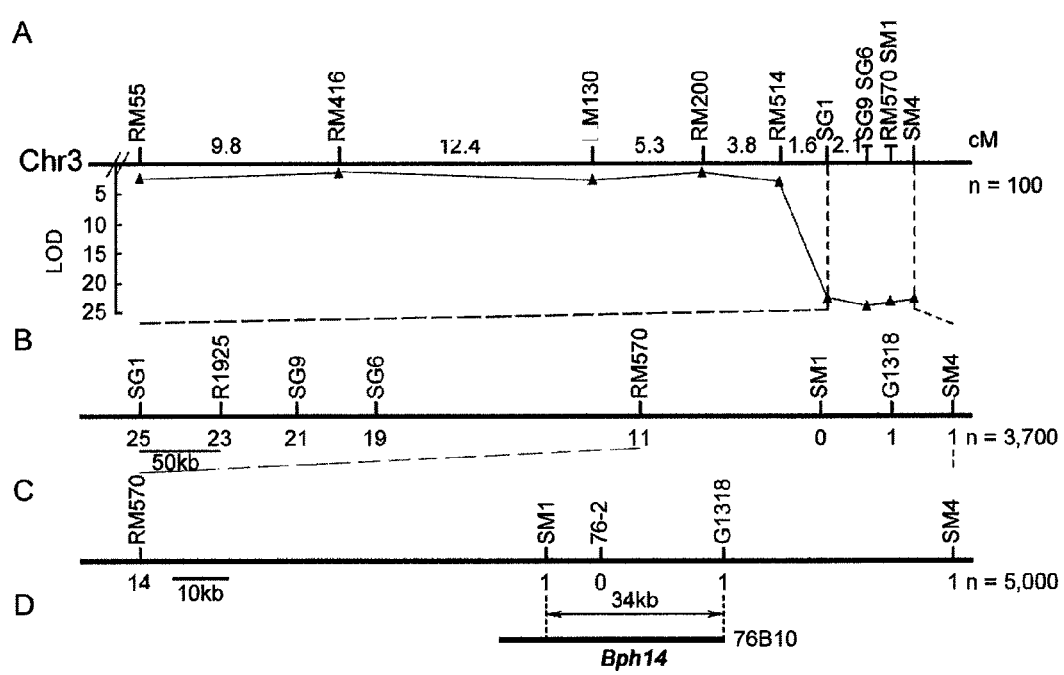
FIG. 1. The positioning of the brown planthopper resistance major gene Bph14 in the $3^{rd}$ chromosome of rice variety B5. A, the scanning result of QTL. Horizontal lines represent the $3^{rd}$ chromosome of rice, and perpendicular short lines represent molecular markers in the chromosome. The values between markers indicate the genetic distance (cM) between markers. Triangles represent the LOD value of each marker. LOD higher than 2.0 represents the existence of one QTL. "n" is the number of single plants in the population; B, the result of $F_2$ recombinant single plants screening using SG1 and SM4. The results from phenotypes and genotypes are integrated, and Bph14 cosegragates with molecular marker SM1. The values below the markers represent the number of recombinant single plants between the molecular marker and Bph14. n represents the number of total $F_2$ single plants screened; C, the result of $F_5$ recombinant single plants screening using RM570 and SM4. Bph14 cosegregates with molecular marker 76-2. The values below the markers represent the number of recombinant single plants between the molecular marker and Bph14. n represents the number of total $F_5$ single plants screened; D, 76B10 is a BAC clone of B5 genome library. Based on the comparison between its sequence and Nipponbare sequence, 76-2, the primer designed based on the difference between the sequences, cosegregates with Bph14. Bph14 is positioned in the 34 kb region between SM1 and G1318.

B: Results of fine mapping. The numbers between the molecular markers represent the number of single plants with the recombination of the marker and Bph14. Bph14 is between the molecular markers SM1 and G1318.

C: The physical map between SM1 and G1318, Bph14 is located in the 34 kb region between SM1-G1318.

DESCRIPTION OF SEQUENCE LISTING

SEQ ID NO:1 is the nucleotide sequence of Bph14 gene.
SEQ ID NO:2 is the Bph14 cDNA sequence.
SEQ ID NO:3 is the Bph14 protein sequence encoded by SEQ ID NO: 1.
SEQ ID NO:4 and 5 and SEQ ID NO:6 and 7 are pairs of primers used to amplify the Bph14 gene from the genome of B5.
SEQ ID NO:8 and 9 is a pair of primers used to amplify the cDNA of Bph14 gene.
SEQ ID NO:10 and 11 is a pair of primers used to amplify 35S promoter from pCAMBIA1301.
SEQ ID NO:12 and 13 are labeling primers of the Bph14 gene.
SEQ ID NO:14 and 15 are primers for molecular marker SG1.
SEQ ID NO:16 and 17 are primers for molecular marker SG6.
SEQ ID NO:18 and 19 are primers for molecular marker SG9.
SEQ ID NO:20 and 21 are primers for molecular marker RM570.
SEQ ID NO:22 and 23 are primers for molecular marker SM1.
SEQ ID NO:24 and 25 are primers for molecular marker 76-2.
SEQ ID NO:26 and 27 are primers for molecular marker SM4.

DETAILED DESCRIPTION

The following embodiments further illustrate the contents of the present invention, but they should not be understood to limit the present invention. Modifications or substitutions made to the method, process or condition of the present invention, when not deviating from the spirit and essence of the present invention, all are within the scope of the present invention.

If not specifically indicated, the technical means used in the embodiments are routine means well known to the skilled person in the art.

EXAMPLE 1

Positional Cloning of the Bph14 Gene

1.1. Preliminary Mapping Result of Bph14

The brown planthopper resistant rice material RI35 (Hao P Y, Liu C X, Wang Y Y, Chen R Z, Tang M, Du B, Zhu L L, He G C (2008) Herbivore-induced callose deposition in the sieve plates of rice: an important mechanism for host resistance. Plant Physiology 146: 1810-1820) was crossed with a rice variety sensitive to brown planthopper (Taichung native 1, TN1, bought from national rice seed resource library) to establish the F2 population containing Bph14. In order to evaluate the brown planthopper resistance phenotype of each single plant in the F2 mapping population, the seedling bulk screening test was used to examine the resistance of each single plant in the population. The pest resistance level of single F2 plant is calculated according to the pest resistance level of all single plants of the corresponding $F_{2-3}$ family. Using the methods of PCR (polymerase chain reaction), polyacrylamide gel electrophoresis, RFLP probe and Southern blotting (Sambrook, et al.) the separation state of SSR and RFLP molecular probes was detected of each single F2 plant. Based on the subtype of F2 molecular marker, JoinMap3.0 software (Kyazma B. V., PO Box 182, 6700 AD Wageningen, Netherlands) was used to establish the molecular marker genetic linkage map of the rice chromosome. With the assistance of the quantitative character analyzing software MapQTL5.0 (Kyazma B. V., PO Box 182, 6700 AD Wageningen, Netherlands), interval mapping analysis was combined with the quantitative data of brown planthopper resistance phenotype collected in the seedling bulk screening test. The results indicate: a QTL peak value exists between the $3^{rd}$ chromosome molecular markers R1925 and G1318, the LOD value reaches 49.3 and the contribution rate to the phenotypic variance is 90.6%.

1.2 Fine Mapping of Bph14

Based on earlier results, the methods of PCR (polymerase chain reaction) and polyacrylamide gel electrophoresis are used to screen the F2 population with two SSR markers RM514, located outside of R1925 and G1318, and SM1, located within R1925 and G1318, to get 54 recombined single plants. Integrating the molecular markers of recombinant single plants, the single plants having identical molecular markers and the same level of pest resistance were pooled (Table 1). Except from the single plant SA69, the 12 single plants RT25-RT15 have identical phenotype with the molecular marker SM1, but in SA69, the phenotype is identical with G1318. Thus, Bph14 is located between SM1 and G1318.

TABLE 1

The pest resistance performance of recombined F2 single plants

| No. of single plant | RM514 | SG1 | R1925 | SG9 | SG6 | RM570 | SM1 | G1318 | Phenotype | Pest resistance level |
|---|---|---|---|---|---|---|---|---|---|---|
| RT1 | R | R | R | R | R | R | H | H | H | 5.6 |
| RT5 | R | R | R | R | R | H | H | H | H | 4.74 |
| RT16 | R | R | H | H | H | H | H | H | H | 5.83 |
| RT2 | R | H | H | H | H | H | H | H | H | 5.49 |
| SA50 | R | H | H | H | H | H | R | R | R | 3.93 |
| SA74 | H | H | H | H | H | H | R | R | R | 3.96 |
| SA55 | S | H | H | H | H | R | R | R | R | 3.86 |
| RT18 | H | H | H | H | H | R | R | R | R | 4.04 |
| RT83 | H | H | H | H | R | R | R | R | R | 4.56 |
| RT82 | H | H | H | R | R | R | R | R | R | 4.1 |
| RT10 | H | R | R | R | R | R | R | R | R | 4.43 |
| RT25 | H | H | H | S | S | S | H | H | H | 4.88 |
| SA51 | H | H | S | S | S | H | H | S | H | 4.48 |
| SA66 | H | H | S | S | S | H | H | S | H | 4.78 |
| SA69 | S | S | S | S | S | H | H | S | S | 7.38 |
| RT84 | H | H | H | H | H | S | S | S | S | 7.23 |
| RT24 | H | H | H | H | H | S | S | S | S | 8.55 |
| SA60 | H | H | H | S | S | S | S | S | S | 7.55 |
| RT3 | H | S | S | S | S | S | S | S | S | 8.25 |
| SA102 | S | S | S | S | S | S | S | H | S | 8.32 |
| RT8 | S | S | S | S | S | S | H | H | H | 5.58 |
| RT7 | S | S | S | S | S | H | H | H | H | 5.39 |
| RT17 | S | S | S | S | H | H | H | H | H | 4.35 |
| RT15 | S | H | H | H | H | H | H | H | H | 4.96 |

R = resistant, H = heterozygous, S = susceptable.
The top axis of Table 1 indicates the molecular marker screened.

1.3. Construct the Brown Planthopper Resistance Genomic Library

For the preparation of plant high molecular weight genomic DNA, see the methods of Zhang Hongbin et al. (Zhang et al., Preparation of megabase DNA from plant nuclei. Plant J 1995, 7, 175-184). Nuclei from the young leaves of brown planthopper resistance rice B5 (Wang B N, Huang Z, Shui L H, Ren X, Li X H, He G C (2001) Mapping of two new brown planthopper resistance genes from wild rice. Chinese Science Bulletin 46: 1092-1095) was extracted and embedded in low-melting point agarose. An appropriate amount of restriction enzyme BamHI was added to the embedded nuclei for partial digestion. Pulsed field gel electrophoresis was performed with the CHEF Mapper pulsed field electrophoresis system to isolate the needed fragment. The strongest gel band from the region containing the 50-250 kb fragment was cut out and placed into the dialysis bag. The DNA fragment was recovered using electroelution (Strong et al., Marked improvement of PAC and BAC cloning is achieved using electroelution of pulsed-field gel-separated partial digests of genomic DNA. Nucleic Acids Res. 1997, 25, 3969-3961). The large fragment DNA isolated with electroelution was collected and put into a 1.5 ml centrifuge tube, 600 ng recovered DNA fragment (50-250 Kb) was mixed with 200 ng dephosphorylated vector BIBAC2, incubated at 60° C. for 10 min and cooled to room temperature. T4 DNA ligase was added and the mixture was incubated at 16° C. for 16 h. Taking 2 μl ligation product and 40 μl DH10B competent cells, the Gene Pulser system was used to perform electrotransformation. The transformed cells were plated onto agarose containing 50 mg/l Kanamycin and incubated at 37° C. overnight. Positive clones were picked from the plate and inoculated into a 384 well cell culture plate containing 70 μl medium, and incubated at 37° C. for 30 h. After the construction of the library, two copies were made with Genetix Q-PIX and one perserved at −80° C. In order to estimate the distribution of the length of the inserted fragment and the volume of the clones, 30 BIBAC clones were randomly picked from the library, and their plasmids extracted by alkaline lysis. After digesting with appropriate amount of NotI, the length of the inserted fragment was confirmed with pulsed field gel electrophoresis (Shi Z Y, Ren X, Weng Q M, Li X H, He G C (2003) Construction of genomic library of a BPH-resistant rice line with binary vector and physical map of Qbp1 locus. Plant Science 1165:879-885).

1.4. Construction of the Physical Map of the SM1-G1318 Region.

Figure 3:
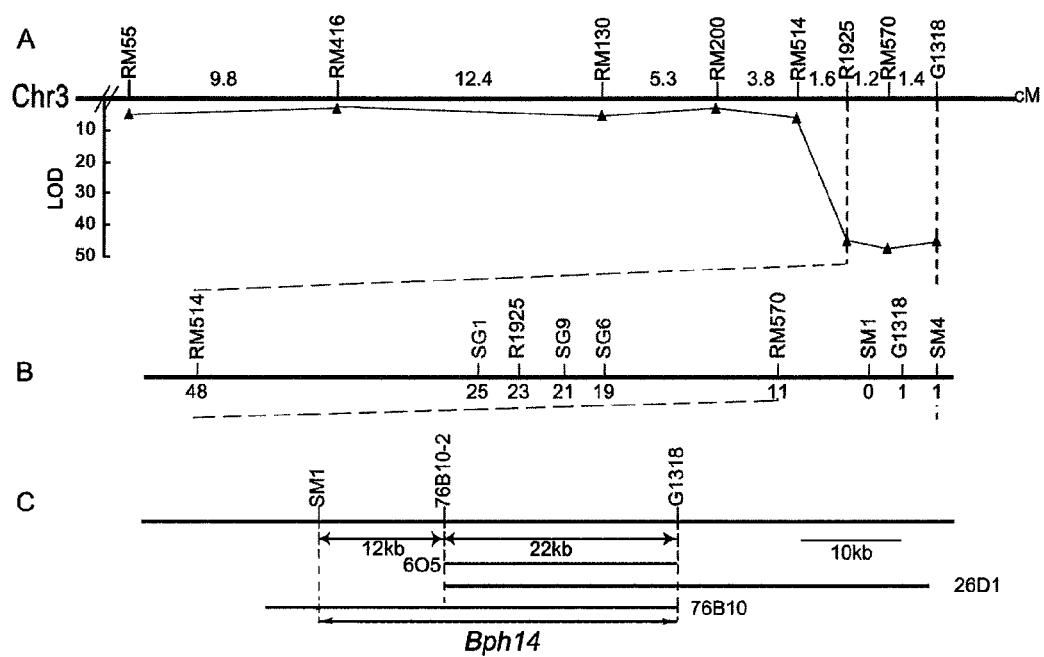
FIG. 3. Mapping of Bph14. A: The result of Bph14 preliminary mapping. The name of the markers are above the chromosome, the numbers represent the genetic distance (cM) between the markers, the QTL scanning result shows that there is a biggest LOD value 49.3 between the molecular markers R1925 and G1318.

All the BAC clones were screened for the R1925-G1318 region. After double digestion with BamHI and EcoRI, electrophoresis was performed and the nucleic acid fragments were transferred to a membrane. Then, the end of the digested clone was labeled with radioactive $\alpha$-$^{32}$P-dCTP. Southern blotting with the BAC clones was performed as before, and the BAC clones which have overlaps and the length of the overlapped fragment based on the hybridization signal were identified. Based on the results, the physical map was constructed (FIG. 3C). For the terminal isolation of BAC positive clones, see the TAIL-PCR method invented by Liu Yaoguang et al. (Liu and Whittier, Thermal asymmetric interlaced PCR: automatable amplification and sequencing of insert end fragments from P1 and YAC clones for chromosomewalking. Genomics 25: 674-681). The results of the screen and TAIL-PCR show that the BAC clone 76B10 contains the complete Bph14 gene (FIG. 3C).

1.5. Analysis of Candidate Genes in the SM1-G1318 Region

Sequence analysis for the entire sequence of the Bph14 gene containing clone was performed; the NCBI database was searched using this sequence as the target sequence to identify the homologous sequence of the Nipponbare genome in this region. RiceGAAS online software (Sakata, K., Nagamura, Y., Numa, H., Antonio, B. A., Nagasaki, H., Idonuma, A., Watanabe, W., Shimizu, Y., Horiuchi, I., Matsumoto, T., Sasaki, T. & Higo, K.: "RiceGAAS: an automated annotation system and database for rice genome sequence", 2002. Nucleic Acids Res., 30: 98-102) was used to perform gene prediction and annotation, also ClustalW was used for comparative analysis (table 2).

TABLE 2

Comparison of the predicted pest-resistant rice genes in the region of the Bph14 gene with the predicted genes of Nipponbare

| the predicted genes of Nipponbare | | | | the predicted pest-resistant rice genes | | | | |
| --- | --- | --- | --- | --- | --- | --- | --- | --- |
| NO: | Predicted function | Number of amino acid | Number of exon | NO: | Predicted function | Number of amino acid | Number of exon | Similarity (%) |
| g1 | Putative ARPC protein p20 | 75 | 2 | g1 | Putative ARPC protein p20 | 75 | 3 | 100 |
| g2 | Putative B cell receptor related protein 31 | 217 | 3 | g2 | Putative B cell receptor related protein 31 | 189 | 2 | 94.7 |
| g3 | Putative reverse transcription transposon | 1997 | 4 | | | | | |
| g4 | Putative NO inducing protein NOI | 238 | 4 | g3 | Putative NO inducing protein NOI | 246 | 4 | 96.6 |
| | | | | g4 | putative disease-resistant protein | 1333 | 2 | 83.4 |
| | | | | g5 | Putative RPM1 interacting protein RIN4 | 148 | 4 | 33.8 |
| g5 | Putative disease-resistant protein | 1315 | 1 | g6 | Putative disease-resistant protein | 1121 | 3 | 99.6 |
| g6 | Unknown protein | 15 | 2 | g7 | Putative protein | 148 | 3 | |
| g7 | Unknown protein | 132 | 2 | g8 | Putative protein | 115 | 3 | |
| g8 | Putative RPM1 interacting protein RIN4 | 168 | 3 | g9 | Unknown protein | 223 | 3 | |
| g9 | Unknown protein | 49 | 2 | | | | | |
| g10 | Putative protein | 87 | 2 | | | | | |
| g11 | Putative disease-resistant protein | 680 | 2 | g10 | putative disease-resistant protein | 680 | 2 | 99.7 |

By comparing the predicted genes of the two, it was found that the disease resistant protein encoded by the 4$^{th}$ gene of the pest resistance rice is quite different from that of Nipponbare. Now, it is commonly considered that the sucking and eating of rice by piercing-sucking insects is similar to the process of rice infection by pathogenic bacteria, therefore, the mechanism of rice to resist piercing-sucking insects might be the same as that of resisting pathogenic bacteria. Thus, this gene can be determined to be Bph14.

1.6. Screening the cDNA Library

Using the predicted gene corresponding to the EST as a probe, phage in situ hybridization with the cDNA library of brown planthopper induced pest-resistant rice B5 was performed (Wang X L, Weng Q M, You A Q, Zhu L L, He G C (2003) Cloning and characterization of rice RH3 gene induced by brown planthopper. Chinese Science Bulletin 48: 1976-1981). After three rounds of in situ hybridization, two chosen phage clones with PCR were examined, and afterwards the length of the inserted fragment was determined with enzyme digestion. Full length cDNA was sequenced. Its nucleotide sequence is as shown in sequence listing, SEQ ID NO:2. However, the skilled person in the art will understand that according to the nucleotide sequence disclosed in the present invention, by designing appropriate primers, the Bph14 gene can be amplified and obtained from the genome of brown planthopper resistance rice. For example, primers: 5' ctccctgactgaagaagagaagag3' (SEQ ID NO: 4) and 5' tgctagagtgattacttatgatg3' (SEQ ID NO: 5), the sequence can be obtained by using long fragment PCR amplification kit and amplifying the genome of brown planthopper resistance rice or wild rice (94° C. for 2 minutes; 30 cycles of 94° C. for 15 seconds, 58° C. for 30 seconds, 72° C. for 7 minutes; 72° C. for 2 minutes).

EXAMPLE 2

Functional Verification of Bph14 and its Application 2.1. Construction of Genetic Transformation Vector The vector used is pCAMBIA1301 (bought from Australia Center for the Application of Molecular Biology to International Agriculture). Based on the result of genome sequencing, primers were designed (5'cgg aattcctccctgactgaagaagagaagag3' (SEQ ID NO: 6), 5'cgg aattctgctagctgtgattctcttatgatg3' (SEQ ID NO: 7) that contain an EcoRI linker. Using these primers, the genome of pest-resistant rice B5 was amplified as described below (Z. Huang et al., Identification and mapping of two brown planthopper resistance genes in rice. *Theor Appl Genet*, 2001, 102: 929-934). The total volume of PCR reaction is 50 µl, 1 µl DNA, 10× buffer 5 µl, 10 mM dNTP 1 µl, 10 mM primers each 3 µl, high-fidelity Taq enzyme 1 U; reaction program: 94° C. 2 min, 94° C. 15 s, 58° C. 30 s, 72° C. 7 min 30 s, totaling 30 cycles. The product was purified by adding ⅒ volume 3 mM NaAC and 2× volume absolute alcohol. The obtained sequence contains a 1960 bp promoter and 4997 bp genomic sequence upstream of Bph14, and downstream 436 bp 3' non-translational region, which was digested with EcoRI, where the total volume the digestion system was 20 µl: about 5 µl (1 µg) PCR product, 1× reaction buffer, EcoRI 1 U, mixed well and incubated at 37° C. overnight. The product was precipitated with ⅒ volume 3 mM NaAC and 2× volume absolute alcohol, recovering the needed fragment. The digestion system of pCAMBIA1301 vector is as stated before, purified with the purification kit. The ligation reaction used is as follows: genomic fragment 1 µl, vector 0.5 µl, 2 U T4 ligase, 5× buffer 2 µl, total volume 10 µl, ligate at 4° C. overnight. The ligation product was transformed into *E. coli* DH10B by heat shocking at 42° C. for 90 s, adding in 400 µl LB, recovering for 45 minutes, transferring 200 µl of the culture onto LA plate containing kanamycin, and incubating at 37° C. overnight. Single clones were picked, amplified, and plasmid extracted and tested by enzyme digestion. A positive clone was picked and electro-porated into *Argobacterium* EHA 105. Cloning was confirmed by extracting the plasmid and verified with PCR. The *Argobacterium* culture containing the constructed vector was preserved by taking 750 µl and adding 50% glycerol of the same volume, mixing well. The culture was stored at −70° C.

Primers were designed based on full length cDNA sequence, containing XmaI and XbaI linker (5' tcccccgg-gatggcggagctaatggccac3'(SEQ ID NO: 8), 5' gctctagactact-tcaagcacatcagccta3' (SEQ ID NO: 9)). Total RNA was extracted from B5 leaf sheath using TRIzol of Invitrogen (Invitrogen Corporation, 5791 Van Allen Way, PO Box 6482, Carlsbad, Calif. 92008), then, the cDNA of B5 was obtained by using the reverse transcription kit of Fermentas (Fermentas International Inc, 830 Harrington Court, Burlington Ontario L7N 3N4 Canada); reaction system: total RNA 1 µg, oligo(dT) 1 µl, 5×buffer 4 µl, inhibitor 1 µl, 10 mMdNTP 2 µl, reverse transcriptase 1 µl, incubate at 42° C. for 1 hour. B5 cDNA was amplified using the designed primers. The PCR reaction system is as described above, however, in the program, elongate at 72° C. for 4 min to get the cDNA sequence of Bph14. Meanwhile, the promoter required for cDNA transcription can be obtained from PCR amplification of the 35S promoter present in pCAMBIA1301. Using the designed primers containing EcoRI and XmaI linker (5' cggaattcatg-gtggagcacgcacactct3' (SEQ ID NO: 10), 5' tcccccgggatctcat-tgcccccgggat3' (SEQ ID NO: 11)), the 35S promoter sequence was amplified from pCAMBIA1301. The PCR reaction system used is as described above, however the elongation time is 1 min. The 35S promoter and the pCAMBIA1301 vector were digested with EcoRI and XmaI each. The 35S fragment and the linearized vector were ligated and transformed into *E. coli* after recovery. The obtained positive clone and the Bph14 cDNA sequence was digested with XmaI and XbaI each, the products were recovered, ligated and transformed. A 35S:Bph14 vector was constructed and electro-porated into *Argobacterium* EHA 105, the detailed process is described above.

2.2 Genetic Transformation

The above mentioned Bph14 genomic transformation vector and cDNA transformation vector were separately introduced into the ordinary rice variety Kasalath (bought from national rice seed resource library or national rice research institute) sensitive to brown planthopper using the genetic transformation method mediated by *Argobacterium* EHA 105 (Hiei et al., 1994, Efficient transformation of rice (*Oryza sativa* L.) mediated by *Argobacterium* and sequence analysis of the boundaries of the T-DNA. *Plant Journal* 6:271-282). At the same time, a blank vector (pCAMBIA1301) was used as a negative control.

2.3 The Expression Result of Bph14 Gene and its Application 14 cultured seedlings, obtained from each of the two transformed lines above, and 4 control seedlings, were planted in the field. After harvesting the T1 generation separately, homozygous plants (14 plants each) were selected for the pest resistance test. After the pest resistance test at the seedling stage and at mature stage, in both cases, the brown planthopper resistance of transgenic plants is evidently increased, while the control plants have no resistance against brown planthopper. All the pest resistance level of transgenic rice at seedling stage is between Grade 3-5, as determined by the process set forth in Huang, et al. (Huang Z et al, 2001 Identification and mapping of two brown planthopper resistance genes in rice. *Theor. Appl. Genet.* 102, 929-934). The transgenic plants at mature stage are in good condition after the addition of pests and they can set seeds normally. At the same time, EPG (Peiying Hao et al, Herbivore-induced callose deposition on the sieve plates of rice: an important mechanism for host resistance. PlantPhysiol, 2008, 146: 1810-1820) showed that when brown planthoppers feed on transgenic plants, evidently less time is spent on phloem. The test of honeydew method (P. Paguia, Honeydew excretion measurement techniques for determining differential feeding activity of biotype of *Nilaparvata lugens* on rice varieties. J. Econ. Entomol, 1980, 73: 35-40) proved that the amount of excretion egested by brown planthopper fed on transgenic plants decreased. Thus, the cloned Bph14 can cause resistance of the rice against the feeding of brown planthoppper on rice.

EXAMPLE 3

Figure 2:
FIG. 2. The electrophoresis graph of single plants examined with the SSR marker 76B10-2. The first two lanes are the pest-resistant parental plant RI35 and the pest-sensitive plant TN1, the rest shows the genotypes of single plants of the F2 population.

Molecular Marker Assists the Selection of Bph14 Carrying Brown Planthopper Resistance Rice 3.1 Based on the genomic sequence and cDNA sequence of Bph14 gene, multiple pairs of primers of SSR marker or STS marker can be designed. In the present embodiment, the pair of primers 5' ctgctgctgctctcgtattg3' (SEQ ID NO: 12), 5' cagggaagctccaagaacag3' (SEQ ID NO: 13) is used as labeling primers for the selection of rice with pest resistance. The length of the amplified fragment is 172 bp. By performing PCR amplification, using primers designed on the Bph14 gene sequence, one can test for the presence of the molecular marker by polyacrylamide gel electrophoresis. The cross-breeding offspring plants showing the same PCR bands as pest-resistant rice (amplification product contains a 172 bp fragment) are the selected plants containing Bph14 gene (FIG. 2). The pest resistance of these plants is confirmed with seedling bulk screening test and test at mature stage. Brown planthopper resistance rice is bred through self cross and economical character selection of these plants.

3.2 One can evaluate brown planthopper resistance of the mapping population by using the seedling bulk screening test: F3 seeds were harvested from the F2 plants, and approximately 20 seedlings (called one family) were grown in a tray. Resistant control variety RI35 and sensitive control variety TN1 were grown together. Once the plants developed approximately 2-3 leaves, the plants were inoculated with 2nd-4th instar brown planthopper nympha (10 nympha/plant) and the state of damage was recorded in each of the families when all sensitive control TN1 plants were dead. The experiment was repeated for 3 times with each material. According to the results of pest resistance evaluation, the families of the mapping population were classified as to their pest resistance level.

EXAMPLE 4

More Molecular Markers for Determining Brown Planthopper Resistance Genotype 4.1. The Construction of RI35/TN1 $F_2$ Population and Phenotype Evaluation Using art recognized methods (Wang B N et al, 2001 Mapping of two new brown planthopper resistance genes from wild rice. *Chinese. Sci. Bull.* 46, 1092-1095, Huang Z et al, 2001 Identification and mapping of two brown planthopper resistance genes in rice. *Theor. Appl. Genet.* 102, 929-934), the dominant brown planthopper resistance gene Bph14 was found to be located at the end of the long arm of the rice $3^{rd}$ chromosome, and its RFLP marker is between R1925 and G1318. Due to the high difficulty of the RFLP technique, a huge amount of work is required in large-scale breeding and screening.

In order to search for simple and efficient molecular markers that had tighter link with Bph14, we chose the brown planthopper resistant variety RI35 which originated from the $7^{th}$ generation of recombinant inbred line between B5 and Minghui 63, only carrying brown planthopper resistance major gene Bph14 (Ren X et al, 2004 Dynamic mapping of quantitative trait loci for brown planthopper resistance in rice. *Cereal. Res. Commun.* 32, 31-38). Hybrids were produced using RI35 as the female parent and brown planthopper susceptible rice variety. TN1 as the male parent. RI35/TN1 $F_2$ segregation population was constructed. RI35/TN1 $F_{2:3}$ lines were respectively obtained from each $F_2$ single strain by inbreeding.

Resistance evaluation of parent plants and $F_{2:3}$ lines was conducted with introduction during seedling stage. To ensure that the parent plants and each line from the $F_{2:3}$ population grow at the same rate, all experimental materials were respectively soaked and hastened to germinate before the seeding. 20 seeds from each line (variety) were seeded in a 54 cm long, 35 cm wide and 8 cm high bread box filled with nutrient soil. 40 materials were seeded in each box, including 2 resistant parent plants and 4 susceptible parent plants. Thinning was conducted seven days after seeding. Sick and weak seedlings were discarded, and at least 15 plants were kept in each cup. When the seedlings reached three-leaf stage, they were inoculated with 2~3 instar brown planthopper larvae at the ratio of 8 per seedling, and were covered with nylon mesh. When the susceptible variant TN1 died out, each single strain was evaluated for resistance at grade 0, 1, 3, 5, 7 and 9 (Table 3) according to the method described by Huang et al (Huang Z et al, 2001 Identification and mapping of two brown planthopper resistance genes in rice. *Theor. Appl. Genet.* 102, 929-934), and the resistance grade of each line from the parent plants and the population was calculated by weighted mean, and the single strain genotype was estimated from the resistance grade.

TABLE 3

| The classing criteria of brown planthopper resistance and susceptibility used in the present study | | |
|---|---|---|
| Grade | Severity of Injury (Evaluated when more than 90% Taichung native 1 died) | Resistance Level |
| 0 | Healthy plant, no injured leaf | Resistant (R) |
| 1 | One yellow leaf | Resistant (R) |
| 3 | One or two yellow leaves, or one withered leaf | Medium Resistant (MR) |
| 5 | Two or three yellow leaves, or two withered leaves | Medium Resistant (MR) |
| 7 | Three or four withered leaves, but plant still alive | Susceptible (S) |
| 9 | Plant dead | Susceptible (S) |

4.2. Molecular Marker Analysis of RI35/TN1 $F_2$ Population

DNA of the parent plants and each line of $F_2$ population was extracted using CTAB technique (Murray M G & Thompson, 1980 Rapid isolation of high-molecular-weight plant DNA. *Nucleic Acids Res* 8: 4321-4325).

Since R1925 and G1318 locate respectively in 32G11 and 96M04, BAC clones of Nipponbare rice genome, we conducted a search for SSR motifs in the sequences of these two BAC clone using the search tool SSRIT described by Temnykh, et al. (Temnykh S, DeClerck G, Lukashova A, Lipovich, Cartinhour S, McCouch S. Computational and experimental analysis of microsatellites in rice (*Oryza sativa* L.): frequency, length variation, transposon associations, and genetic marker potential. Genome Research. 2001. 11(8): 1441-1452) with the following parameters: maximum motif length was tetramer, the minimum repeat was 5. All SSR motifs longer than 15 bases (motif length×repeat times) were selected and primers were designed based on their flanking sequences as candidate SSR markers.

SSR markers were analyzed in accordance with Temnykh's method (Temnykh S et al, 2000 Mapping and genome organization of microsatellite sequences in rice. Theor Appl Genet. 100: 697-712). The 10 μl reaction system included: 10 mM Tris-HCl pH8.3, 50 mM KCl, 1.5 mM $MgCl_2$, 50 μM dNTPs, 0.2 μM primer, 0.5 U Taq polymerase and 20 ng DNA template. Amplification is conducted using PTC-100 PCR amplifier: 94° C. 2 min; 94° C. 15 sec, 55° C. 30 sec, 72° C. 1.5 min, 35 cycles; 72° C. 5 min. Amplified products were separated using 6% undenatured PAGE gel, and visualized by silver staining (Zhu et al, 2004 Identification and characterization of a new blast resistance gene located on rice chromosome 1 through linkage and differential analyses. *Phytipathology* 94:515-519). Amplified DNA bands were observed using a transilluminator with a fluorescent lamp. The results were recorded. Primers that had polymorphism between parent plants were analyzed in $F_2$ population and population genotype data were obtained.

The genetic map of rice SSR markers was constructed with population genotype data based on the law of linkage and crossover. The software used was MAPMAKER/EXP3.0.

A whole genome scan was conducted using composite interval mapping (CIM) from Windows QTL Cartographer V2.0 software. A segregation analysis between the brown planthopper resistance and SSR markers was conducted using the analytical software MAPMAKER/EXP3.0, and Kosambi functions were converted into genetic distances (cM).

4.3 Screening of RI35/TN1 $F_2$ and $F_5$ Population Using Molecular Markers and Positioning of Bph14 Gene Based on the positioning results of QTL, $F_2$ single plants were screened using the flanking SSR markers SG1 and SM4 to obtain the single plants which had recombination between the two markers. The genotype and phenotype of each single strain were checked as described above to explore which markers cosegregated with the resistance phenotype.

Using molecular marker-assisted selection, we selected $F_2$ single plants which were heterozygous in Bph14 site and preferably derived from TN1 or heterozygous in other sites; After inbreeding, single plants that were heterozygous in Bph14 site and preferably derived from TN1 in other sites were obtained using molecular marker-assisted selection. Eventually, $F_5$ inbred population was constructed, in which except for the Bph14 site, all other regions were from the genome of TN1. Based on the results of (1), $F_5$ single plants were screened using the flanking SSR markers RM570 and SM4 to obtain the single plants which had recombination between the two markers. The genotype and phenotype of each single strain were checked as described above to explore which markers cosegregated with the resistance phenotype.

Based on the results of (2), gene library of B5 was screened, and BAC clones of B5 gene library covering the two markers were obtained. After sequencing, the said sequence was compared for DNA difference with the corresponding sequence of Nipponbare. Primers were designed based on the difference of sequences to amplify the DNA sequence of RI35 and TN1. Primers that have polymorphism were used in the analysis of $F_2$ and $F_5$ recombinant single plants to explore whether they cosegregated with resistance phenotype.

4.4 Results and Analysis

Group introduction test in seedling stage showed that the resistance grade of RI35 and TN1 were 2.7 and 9 respectively, which indicated that RI35 was brown planthopper resistant while TN1 was susceptible. The resistance grade of $F_1$ plants was 3.4, showing resistance against brown planthopper, indicating that the resistance of RI35 was controlled by dominant gene. The frequency distribution of the resistance grade of 100 $F_{2:3}$ lines against brown planthopper showed continuous distribution. The minimum value was 3.0 while the maximum value was 9.0, and three obvious peaks were found at the three locations of 3.5, 5.5 and 8.5. Based on the resistance grade $F_{2:3}$ lines were divided into three phenotypes: resistance, segregation of resistance and susceptibility, and susceptibility. The corresponding genotypes of the $F_2$ single plants were recorded as three types: RR (homozygous resistance), Rr (heterozygous resistance) and rr (homozygous susceptibility). The segregation of resistance and susceptibility of $F_2$ population was in accordance with a 1:2:1 ratio ($\chi^2$=0.54, $\chi^2_{005}$=5.99) (Table 2).

Huang Zhen and Wang Buna have identified two dominant brown planthopper resistance genes, Bph1 and Bph15, from B5, a fertility line of *O. officinalis*. RI35 comprises one brown planthopper resistance major gene Bph14. Therefore, in this study, QTL of the $F_2$ population was positioned using the SSR markers from the $3^{rd}$ chromosome to determine whether it was in accordance with previous studies.

Based on the search results of SSRIT, we selected all the SSR motifs longer than 15 bases (motif length times×repeat times), and designed primers based on their flanking sequences. Depending on the different BAC clones these motifs were situated, these SSR markers were named as SG1, SG2, etc. and SM1, SM2, etc. consecutively. We used these SSR markers to amplify the DNA of the parent plants RI35 and TN1. Only SG1, SG6, SG9 and SM1, SM4 showed polymorphism between parent plants in electrophoresis.

Whereafter we used SSR markers that had polymorphism between parent plants to locate the QTL of the $F_2$ population. The results showed that there was one QTL site between SG1 and SM4 at the end of the long arm of the $3^{rd}$ chromosome, whose LOD value was 25.3 and the contribution rate was 67.5%. Molecular marker SG6 and SG9 cosegregated with Bph14. SG1 was 2.1 cM from Bph14; RM570 and SM1 were 0.8 cM from Bph14; SM4 was 1.5 cM from Bph14 (FIG. 1). The accurate rate of SG1, SG6, SG9, RM570, SM1 and SM4 were 98%, 100%, 100%, 99%, 99% and 98%.

The distance between SG1 and SM4 was large. In sequenced indica rice variety Nipponbare, the distance was 270 kb. Therefore, to search for markers more tightly linked to Bph14, we screened 3700 $F_2$ single plants using SG1 and SM4. The results showed that, only 26 single plants had recombination between marker SG1 and SM4. We used other SSR markers, as well as R1925 and G1318 to check the genotype of the recombinant single plants, and combined with the resistance evaluation results, we found that Bph14 cosegregated with SM1 (Table 5, FIG. 1)

We constructed the inbred $F_5$ population using the method of molecular marker-assisted selection in which other than Bph14 site, all other regions were from the genome of TN1. 5000 $F_5$ single plants were screened using the flanking SSR marker RM570 and SM4, and 15 single plants that had recombination between the two markers were obtained. We checked the genotype of the recombinant single plants, and combined with the resistance evaluation results of recombinant single plants, we found Bph14 located between SM1 and SM4. G1318 was used to check the genotype of these recombinant single plants, and eventually Bph14 was positioned between SM1 and G1318 (Table 6, FIG. 1). Through screening the gene library of B5, 76B10, a BAC clone covering both markers was obtained. After sequencing, the sequence was compared for DNA difference with the corresponding Nipponbare sequence, and primers named 76-1, 76-2 etc. were designed based on the difference of sequence to amplify the DNA sequence of RI35 and TN1. Eventually only 76-2 had polymorphism between RI35 and TN1. The obtained single plants were analyzed by 76-2, and it was found that 76-2 cosegregated with Bph14.

The results showed that, the molecular markers described above have few recombinant single plants with Bph14, therefore they are useful to detect the existence of Bph14 resistance major gene, and brown planthopper resistant rice varieties can be obtained using the method of molecular marker-assisted breeding so that the progression of breeding brown planthopper resistant rice varieties in China can be expedited.

TABLE 4

The resistance-susceptibility segregation ratio against brown plant hoppers in 100 single plants from RI35/TN1 $F_2$ segregation population

| $F_2$ genotype[a] | $F_2$ number of individuals[b] | Corresponding phenotype of $F_{2:3}$ lines[c] |
|---|---|---|
| RR | 23 | RS ≤ 4 |
| Rr | 49 | 4 < RS < 7 |
| rr | 28 | 7 ≤ RS |

[a]RR homozygous resistance; Rr heterozygous resistance; rr homozygous susceptible;
[b]1RR: 2Rr: 1rr Suitability value $\chi^2 = 0.54$, $\chi^2_{0.05} = 5.99$;
[c]Resistance grade: RS, Resistance Score

TABLE 5

The genotype and phenotype of the $F_2$ recombinant single plants screened by molecular markers

| NO: of Single Plants | SG1 | R1925 | SG9 | SG6 | RM570 | SM1[a] | G1318 | SM4 | Phenotype | Resistance Grade |
|---|---|---|---|---|---|---|---|---|---|---|
| RT1 | R | R | R | R | R | H | H | H | H | 5.6 |
| RT5 | R | R | R | R | H | H | H | H | H | 4.74 |
| RT16 | R | H | H | H | H | H | H | H | H | 5.83 |
| SA50 | H | H | H | H | H | R | R | R | R | 3.93 |
| SA74 | H | H | H | H | H | R | R | R | R | 3.96 |
| RT18 | H | H | H | H | R | R | R | R | R | 4.04 |
| RT83 | H | H | H | R | R | R | R | R | R | 4.56 |
| RT82 | H | H | R | R | R | R | R | R | R | 4.1 |
| SA51 | H | S | S | S | H | H | S | S | H | 4.48 |
| RT84 | H | H | H | H | H | S | S | S | S | 7.23 |
| RT24 | H | H | H | H | S | S | S | S | S | 8.55 |
| SA60 | H | H | S | S | S | S | S | S | S | 7.55 |
| SA102 | S | S | S | S | S | S | H | H | S | 8.32 |
| RT8 | S | S | S | S | S | H | H | H | H | 5.58 |
| RT7 | S | S | S | S | H | H | H | H | H | 5.39 |
| RT17 | S | S | S | H | H | H | H | H | H | 4.35 |

[a]From this table we can find that the molecular marker SM1 cosegregates with the resistance phenotype. This result shows that Bph14 locates between molecular marker RM570 and G1318 and cosegregates with SM1

TABLE 6

The genotype and phenotype of the $F_5$ recombinant single plants screened by molecular markers

| NO: of Single Plants[a] | RM570 | SM1 | 76-2[b] | G1318 | SM4 | Phenotype | Resistance Grade |
|---|---|---|---|---|---|---|---|
| RT40-9 | S | R | R | R | R | R | 3.63 |
| RT85-1 | S | R | R | R | R | R | 4.56 |
| RT87-4 | R | S | S | S | S | S | 8.66 |
| RT84-5 | R | S | S | S | S | S | 7.75 |
| RT12-5 | R | H | H | H | H | H | 5.65 |
| RT7-8 | S | H | H | H | H | H | 6.07 |
| SA102 | S | S | S | H | H | S | 8.32 |

[a]Numbers of the single plants indicate that $F_5$ populations eventually obtained from these $F_2$ single plants using molecular marker-assisted selection were used to accurately position Bph14.
[b]From this table we can find that the molecular marker 76-2 cosegregates with resistance phenotype. The result shows that Bph14 locates between molecular marker SM1 and G1318 and cosegregates with 76-2.

One embodiment of the present invention provides an isolated nucleic acid molecule comprising a nucleotide sequence that comprises a brown planthopper resistance gene Bph14 selected from the group consisting of SEQ ID NO: 1 and SEQ ID NO: 2. In another embodiment, the nucleotide sequence encodes a polypeptide molecule comprising the amino acid sequence SEQ ID NO: 3. In yet another embodiment, the nucleotide sequence is operably linked to a heterologous promoter.

Another embodiment of the present invention provides an expression vector comprising the isolated nucleic acid molecule comprising a nucleotide sequence that comprises a brown planthopper resistance gene Bph14 selected from the group consisting of SEQ ID NO: 1 and SEQ ID NO: 2. In yet another embodiment, the present invention provides a transgenic plant, plant tissue, or plant cell comprising the expression vector. In still yet another embodiment, the transgenic plant, plant tissue, or plant cell is a monocot. In further yet another embodiment, the transgenic plant, plant tissue, or plant cell is rice.

Yet another embodiment of the present invention provides a method for producing a transgenic plant which expresses a Bph14 gene, comprising the steps of: (a) stably transforming a cell of a plant with a nucleic acid molecule comprising a nucleic acid sequence selected from the group consisting of SEQ ID NO: 1 and SEQ ID NO: 2 to produce a transformed cell; (b) regenerating a transgenic plant from the transformed cell; and (c) growing the transgenic plant wherein the nucleic acid molecule is expressed. In another embodiment, the transgenic plant is a monocot. In still yet another embodiment, the transgenic plant is rice.

Further yet another embodiment of the present invention provides a molecular marker associated with brown planthopper resistance, wherein the molecular marker is selected from the group consisting of: SG1, SG6, SG9, RM570, SM1, 76-2, and SM4. In one embodiment, SG1 is amplified by primers SEQ ID NOs: 14 and 15. In another embodiment, SG6 is amplified by primers SEQ ID NOs: 16 and 17. In yet another embodiment, SG9 is amplified by primers SEQ ID NOs: 18 and 19. In still yet another embodiment, RM570 is amplified by primers SEQ ID NOs: 20 and 21. In further yet another embodiment, SM1 is amplified by primers SEQ ID NOs: 22 and 23. In another embodiment, 76-2 is amplified by primers SEQ ID NOs: 24 and 25. In yet another embodiment, SM4 is amplified by primers SEQ ID NOs: 26 and 27.

Still yet another embodiment of the present invention is a method for determining the presence or absence of brown planthopper resistance in a plant or seed, comprising analyzing genomic DNA from the plant or seed for the presence of a molecular marker linked to a quantitative trait locus associated brown planthopper resistance, wherein the molecular marker is selected from the group consisting of: SG1, SG6, SG9, RM570, SM1, 76-2, and SM4. In another embodiment, the method further comprises analyzing genomic DNA from a plant or seed for the presence of a second molecular marker linked to a quantitative trait locus associated with brown planthopper resistance, wherein the second molecular marker is G1318. In yet another embodiment, the plant or seed is a monocot. In still yet another embodiment, the plant or seed is rice.

Another embodiment of the present invention is a quantitative trait locus associated with brown planthopper resistance, wherein the quantitative trait locus is located in a 34 kb region between a first molecular marker and a second molecular marker on chromosome 3 of rice. In another embodiment, the quantitative trait locus comprises Bph14.

What is claimed is:

1. A nucleic acid comprising a brown planthopper resistance gene (Bph14), the coding sequence of which is set forth in SEQ ID NO: 2, operably linked to a heterologous promoter.

2. The nucleic acid of claim 1, wherein the coding sequence encodes a polypeptide, the amino acid sequence of which is set forth in SEQ ID NO: 3.

3. An expression vector comprising the nucleic acid of claim 1.

4. A cDNA encoding a rice brown planthopper resistance gene the coding sequence of which encodes the amino acid sequence set forth in SEQ ID NO: 3.

5. The cDNA of claim 4, the nucleotide sequence of which is set forth in SEQ ID NO: 2.

6. A vector comprising the cDNA of claim 4.

* * * * *

SEQUENCE LISTING

```
<160> NUMBER OF SEQ ID NOS: 27

<210> SEQ ID NO 1
<211> LENGTH: 9921
<212> TYPE: DNA
<213> ORGANISM: Oryza officinalis
<220> FEATURE:
<221> NAME/KEY: gene
<222> LOCATION: (1)..(9921)

<400> SEQUENCE: 1
cccgggcctt tctccagtat ctccatgatg attgtttgga ttaacagacc tccctggaga      60
tttacccttg cgggcatttt cgaaatactg tgtgtagagg tgttcaccac ggtcttcatc     120
ctcccagctt ccaaatttag gaacttgttt atgctggtag agattaacaa acaagtacca     180
tttgcgttag gcagacagca tatgctgatt gctgaatcta ctacacgggc ttgttgcctt     240
gtcagttgtc atctttcata tgtaacagga aatagtatat aattctagcc taaacaggta     300
ttccatccgt atatttctag attcattagc atcaatataa atatcggaaa tactagaatg     360
acttacattg taaaacagag aaagtatgat tatctaaact ctcagatagt ctattgtaat     420
cattgtatgc atgacatcag cttgtgtcaa agctgcagct ttgttggatc aaccagaatt     480
tactagttct aaaaaaaaca gaatttactt agatcctgct gaaagacttc gggccaatta     540
gaagcccagt atttggccca aaactggtgt aaactacagg cccataatag aaataagttc     600
actggaggtc ccccaactta acaccgagat tttttgagg tcccttaacc ataaaccaga     660
aatgcgtacc cctaaactat gtaaaaccgt caaaaaaaaa aaggtcccga ggcagtatag     720
ttgctcggtt tcgctgacgt ggcatcctag tcagcaaaaa aaattaaaat aaatatgtgg     780
ggcccacatg taagtgagag aaaatggtgt gggcccaca tttctccttt cttttctttt     840
tctcttctct tctctcccga ttttctcgag tgggcgcggc ggcagagggg agagaggtga     900
ccggcggtgg agcggggggtg gtgggagagg ggggctggcg cgacgtcggc ggcgggagaa     960
aaggagagga ggcggctggc gcgacggcga gctcggacgg caacggcggg aggaggagga    1020
ggagaggagg cagtcggcgc tgtaaaacgc gcatgggatg cggcggatga tgtcgagcgg    1080
gacggtgtcc tcatcaccat cttcctcatc gtcatcgcag tctgcgggtg ccgggcgag    1140 cggtttggga gggaggggga ggcggccagc gagcccgttc gagctcgccc ggcctgcgcg    1200
```

```
cgagctcgcc cctcccatag cttggtgtgc tggggacgac gacgaggaaa ggggagaaa      1260 ggaattgacg gccgatgata gcaatggcgg gcgagcgcgg cgccgggctg ctcatgctcg      1320
ccgaccaggc ccccggcttc gccgcactcg tccgccgtgc tcgcccacgc actcgccgac      1380
ctccgctcca cccgccgctc ctgccgcgtg cccgctgccc gccggcctcc ctgactgaag      1440
aagagaagag agaaattaaa gagaagagaa ggagaagaaa agagaagaga agaaaaaaag      1500
atgtgtagct gacatgtggg ccccatgtac ttttttattt ttttgctga ctagaatgcc       1560 acgtcagcga aaccacccat atatactgtc ataggacctt gagtgcatag tttgtgtgag      1620
tttagggata cacatttctc gttttgtagt taagggacct cgtaaaaatc tcgctgttaa      1680
gttgagagac ccctccggtg aacttattcc cccaaatatt ttctccatgc tctgggctca      1740
aacgcactct tggatgggcc gtgtaatcta caccatttct ggcccaatcc aacgaaggta      1800
gctccagact cctaactccg ccgccgcatg cccaatcctc gccggccgcc gctgccatct      1860
cccttccccc accgccaccg tcgccttctc cgttccccca acaaaggctc agtagcagca      1920
gccgcggcgc ggagagcaga ggccttggag ggcctgcaga ggagcgcccg cgtcgacgaa      1980
gacgacatca gcaggcagtg gacatggcga ctgcgaatgc tatcgccgac gtgggagctt      2040
caggcgagga tgcgtggcct tcatcagctg ctgctcccctt acctgctctg gtttgtcatt      2100
gtgttggttc gtggtttggg gatatcagga tggggaaggg gaatgggttt cgtgccatgt      2160
tgttctattg tgcaatttga tgttctcttg tcgaatttca tggtgattca atctgcatct      2220
gtgttattgg ttgtcaagca aacattttat ttctttcgag atgggtgttt catctgaaat      2280
tggtgtgtct gatgatgtga ccttgtgcaa atcattgttt cattttcttc tattccacag      2340 agatttttt gtttagagtt tattctacca tcttcttacc ttttgaatgc tatgcaccac       2400
agatttctga tttttacaca ttcaatcaca gtgccgaccc ttggcgaatt taaaattttc      2460
tcaccgtcaa aatttaatca aacatctgat ctaacagtag tagcgccagc acggctggta      2520
tttaaggcag aaagaaaggt tgcgagggcg aggagttggt gatgatctgc cggtcgtgtc      2580
gtgactttag gctataaaag atagctgttt ggattaaccc aaccaatgaa gcgaatcatc      2640
gatggccgat agcgagatta tatccaacta atgaagagaa tcaactttaa tcttttgtga      2700
gctacaagtt tcgtggtgaa ggcatatact aataccacca tcatggctgc agcgaatcaa      2760
cgagatgcat ttgtcttgca catttcccac cggatacttt gccatccatg gctttatctc      2820
ctccatgatt gtatccccctt cttcctcaac aaggaacgat cgatcattgt ttgcttcttt      2880
ctctgacgac acttttggtgc aagtgaaagg ctctttcctg gaactcgtcc cgtgagctcc      2940
ttcctggcta catcctcctt aattccttgc cgatttccgg cttcgtcttc actatcgtca      3000
gttcatttct cccgctctgc ctgagagtcc agtttcttgg agatagtcgc cggcttgctc      3060
tctctctctc tctcccttct catcgccagc tccagctcac aatccgagct tacgtggtgg      3120
aatcgctatc gccacctctc ggaagattat tgtactttgc cttgcctact tcttgagtcc      3180
gatcaaacac atccatcatg catctgtttg tacttgcatt cagccaaaca cttccagttt      3240
aactccgtcc gcaagtcaat acttgcattc aatttccatt tcctacaaaa gcagctgctc      3300
agactcttgc cttctccacc cagcaatcgt gtttccttcc ctgtatcctg cgcgtgtgtt      3360
cttagctgct ctaggggatc cttccaatgg cggagctaat ggccaccatg gtggtcgggc      3420
cactgctgtc catggtgaag gacaaggcct ccagctacct cctggagcag tacaaggtga      3480
tggagggcat ggaggagcag cacgagatcc tcaaacgcaa gctgccagcc atcctcgacg      3540
```

```
tcatcgccga cgccgaggag caggcggcta aacacaggga aggggtgaaa gcatggctcg    3600
aggcgctccg gaaggtggcc taccaggcca atgacgtctt cgacgagttc aagtacgagg    3660
cactccgccg caaggccaag gggcactaca agatgctcag cagcatggtt gtaatcaagc    3720
tcattcctac tcacaaccgt attctgttca gttataggat gggcaacaag ctcaggatga    3780
ttctgaatgc cattgaagtt ctaattgaag agatgaatgc ctttaggttt aaattccgac    3840
cagagccacc aatgtcgtcc atgaaatgga ggaagacaga ttctaaaatc tccgaccttt    3900
caaagctaag tgacttagag atatctaaag gcaatcaaca aatatcccta caggcagcca    3960
gcagacatat tacttcattg tccagtctcg ttctgcattt gtccactgat gacacagaaa    4020
cagcatcggt ggccaagcaa caagattcga gtgatttggt gattgaggat gagaaatgga    4080
gtcataaatc tcccctggaa cttatggtct tgagtcggtg caaccttta ttctctcacc    4140 caagtgcact ggctctgtgg acatgttttg ctcagctcct agatctgaaa attcggtatg    4200
ttgatgcgct tgtcagctgg ccagaagagg tgttccaggg cttagtttcc ttgaggaagt    4260
tagagatttc tgtatgcgag aatctgacag gacacacaca agctcgtggg caatctacac    4320
ccgcaccaag tgaactcctg ccacgtttgg agtccctaga gataacgtgt tgtgattcta    4380
ttgtggaggt ccccaatcta ccggcgtctc tcaagctatt agaaattagg gggtgccccg    4440
gcctggagtc catcgtattc aatcagcagc aggataggac gatgttggtg agtgcagaaa    4500
gctttgcaga gcaggataag tcatcgttaa tatcagggtc cacaagcgag accaacgatc    4560
acgtccttcc acgcctagaa tctcttgtaa taaattggtg cgatcgtttg gaggttctcc    4620
atcttcctcc gtccatcaag aaatttggta tttatagctg tgaaaaactt cggtccctct    4680
cagtaaagct ggatgccgtt cgagaattaa gtatcagaca ttgcgggagc ttgaaatcac    4740
tggaatcttg cttaggagag ctcgcgtcgc tgcaacaact caaactttt gattgcaaga    4800 gcctggaatc cttgccgaag gggcctcaag catactcatc tcttacatct cttgaaattc    4860
gtggttgttc tggtataaag gtgcttccac cgagcctaca gcaacgtctg gatgacatcg    4920
aggacaaaga actagatgcc tgctatgaag gtaatcttca gtttcttaac cgtgtaccat    4980
ttagtggtaa aagtttcgag tttcgtgtct agaaccccta gtcaaccatt aatatgatta    5040
tatgtacata gagtacaatg cgcattcata actcacttct gcagctgtgt catctaaacc    5100
cttaaaactt tgagttgcat ttgggtatct aatcgcatgc aaaggaattt agttatatct    5160
cccgtagcca ttccttatat gtgatgatct cttcctgtga ttatgcttgc tagtttggac    5220
tatgtaatta attttgccgg gtgactatgt aattacatga cttcatttag tcgccaggtg    5280
tggcatcatg caattattat ggcaaagctg tattagtcat gatcgaagcc acttggtgaa    5340
cttattccct gctactttga accaatactc attgattatt tccctttaag cgtttgatat    5400
ggacgacagt ttaaatttgc agagctaact aacgcagcgc ttgtctttac atttctctgg    5460
aaactcacag ctccattgca tatgtagttt gagtatacat agtttctttg aactgtctta    5520
tgcctttgaa aagcttgact atggaattct agtctatata ttcaatacat atatttttt    5580 ttcttttgtt tgccagaggc agaagcagaa ccaaagtctc gtcatcgtca atctgcaatc    5640
agtaggctga tgtgcttgaa gtagcagttt caggaccaga tgagagttgt catcatggtt    5700
tgtaacgcgt gcttgatgat tgatttcgaa tgaaattcta gccactatcc ttatgcttac    5760
tctctctatg gtgtgacttc cttgtaggat cgttaccgaa tctgcaattg ttgggttatt    5820
aattgtgtgg ttgtatctca tggtagaatg tattacctac ctacccttc tcaagataaa    5880 ctccagtaaa gtcgatcgtc tggttggtgt gagctgctac aagaaggatg aagccgatga    5940
```

```
tcccaaggcc ttgactttaa gctagtccca ggttgtaagc tgaagaacaa catactggag    6000
cttaaactgc ttcactcttt ttttatcctt ttccttttct tgtgaactgt gatgtgtttg    6060
atctcgttca tgctccatca taagagaatc acagctagca cttccatttc aatgatgttt    6120
ttcctaacat gacatgactg cagaggtaac ttgtgattga tcaacaacat tttgcagcaa    6180
cgttctctcc cgataacgct gcaatggaat tgatcaattg gtgttcctac ttattggaat    6240 cttggacat tgccaacaac tcaagaaagg aagataaaca ggagattgtc agcagattgc    6300
ttgttccagc cagcgaaggg gatctcactg ttcttcccat tgtaggaatg ggggggatgg    6360
gcaagaccac cttagcgcag ctcatttaca atgaccctga cattcagaag catttccagt    6420
tgctgctctg ggtgtgtgtt tccgacaact tcgatgtgga tttgctggct aaaagcatag    6480
ttgaagcagc tcgcaaacag aagaatgata acagtggaag tactaacaag tcaccattgg    6540
atgaacttaa agaagttgtg agtgggcaga ggtacctcct cgttttggat gatgtctgga    6600
accgtgatgc tcgtaagtgg gaagcgctca agtcctacct tcagcacggt ggcagcggta    6660
gctcagtttt gacaacaact cgtgatcaag aagtggctca agtgatggct ccagctcaaa    6720
aaccttatga tctcaagaga ctgaaggaaa gcttcataga ggaaattatc aggacaagtg    6780
ctttcagttc acaacaagaa aggcctcctg agcttctcaa aatggttggt gatattgcca    6840
agaaatgttc tggttcccct ttagctgcaa cagcattggg ctctacactg cgtacgaaga    6900
ccaccaagaa agaatgggag gctatattaa gcagaagcac aatttgcgat gaggaaaatg    6960
gaattttacc aatactcaag ctcagttaca attgcttgcc atcatatatg cggcaatgct    7020
tttccttttg tgcaattttc cccaaggatc atgagattga cgtggaaatg ctgatccagt    7080
tatggatggc caatggtttt atcccagagc aacaaggaga gtgccctgaa atcattggta    7140
aaagaatttt cagtgagttg gtgtcaaggt cattttttca ggatgcgaaa gggatcccgt    7200
ttgagttcca tgatataaag aactctaaga ttacttgtaa gatccatgac cttatgcatg    7260
atgttgcaca atcctccatg ggaaaagaat gcgctgctat agatacagaa gttagtaaaa    7320
gtgaggattt tccttattct gctcgccatc tattttttgtc aggtgataga ccagaagcta    7380
ttcggactcc ttccccagag aaaggatatc caggtatcca aacattaata tgttcacgtt    7440
tcaaatattt gcagaatgta tcaaaataca ggtcattgcg agtattaaca acgatgtggg    7500
aaggttcatt cctgatacca aaatatcatc atcacctgag gtatcttgat ctctcagaaa    7560
gtgaaattaa agcacttcct gaagacataa gcatcctata tcatttgcaa acattgaacc    7620
tttcccgttg tttatctctc cgtcgacttc caaagggaat gaagtacatg accgccctcc    7680
gtcacttgta cactcacgga tgttggagtt taggaagcat gcctcctgac ctcggacacc    7740
tcacttgcct acagacgctt acatgctttg tagccggtac ttgctctggc tgcagtgatt    7800
tgggagagct gcggcagttg gaccttggtg gtcgactaga gctaagaaaa ctggaaaatg    7860
tgacaaaagc tgatgcaaaa gcagcaaatc tcggaaagaa ggaaaaactg accaaattga    7920
ccttaatatg gactgatcag gagtacaagg aggcacagag taataatcat aaagaggtgc    7980
tggaaggtct cacgcctcac gaggggctca aggttctgag tatatatcac tgtgggagca    8040
gtacatgtcc aacttggatg aataaactgc gggacatggt ggggcttgag ttaaatggtt    8100
gcaaaaatct cgagaagctt cctccgttgt ggcagctacc ggctctacaa gttctttgcc    8160
tggaaggact gggtagttta aattgcttgt tcaactgtga cacacacaca cccttcacat    8220
tttgcagact gaaggagcta accttgtctg atatgacaaa ttttgagaca tggtgggaca    8280
```

-continued

```
caaatgaggt acaaggagaa gagctgatgt ttcctgaggt tgaaaagctg tcaatcgaaa      8340
gttgccatag gctaactgcc ttgccaaaag catcaaatgc gatttcagaa tcgtccggcg      8400
aagttagcac cgtgtgtcgt tctgcatttc cagcattgaa ggaaatgaaa ttatatgatt      8460
tgcgtatctt tcagaaatgg gaggcagtcg atggaactcc aagggaggag caacatttc      8520 ctcagcttga caaattagaa atcagacagt gcccagagct gactactcta cctgaagcac      8580
gaatttccca ttgtggaata aaatggaaag attggtacaa tctgctgaaa atgaactgt      8640 cgttactcaa gttgaaacat gtgtcatgtg tgtaactatc agaattgttc tcgacaaaat      8700
cgttgggact tgcaaggtaa aaaaaaaaaa ttcctcagct ctgtaaatgc tattgctgaa      8760
ctaaagttca gaaagctata gtgccgaaag atctcagatg cctactgca acaaaattca      8820 gtacaaatgc aaaacaatgt aacattacgt ggcccagccc atcatggtaa gcccatactg      8880
tatgcgctgc aaactaatat tagttcaggc aattactctg aaatttctga tagacgaacc      8940 tgatttttc atgtcaggtg ccgtgcttgt tcagattcag caacttacat ttccaaagaa      9000 gaaaaggaa attcataccct tctctttatt tggtttttaa aagtggcctg gattttcatt      9060
atttggttaa aatttggcct ttgtcgtaag gatttggatc ctctatccaa acacatgcct      9120
tccaagataa acgaatccct cattatacaa aaaaaaaagc acaagatgct caacaagaag      9180
cttcaaattc gtgtaaatac atgtcatgtc tcgctaccaa acaatatctc aacaatgaca      9240
acagattgga ggtattcatc tcacaatgat acatttcaac acaaatttat gtaggcctcg      9300
ctgacaggac ttggctggat ggctgtcagt tcagttcttg aaccaactga agcatgagca      9360
gccctgcaag gaagcgataa actgaattaa aataggaatt tgttacacaa tacctgtaaa      9420
gtggattaca ttaaaatatt accaaatcat actgtaagca atcatacagt acaagattcc      9480
ttgcaaacaa ccctaaccaa acttctagta aaaccattat tttttctgta gtaccaactt      9540
tttgcaacca ctatatactc cagtaaaaac cagaagtatt gttgcaatga ctttgccgat      9600
aaattataga acgcggctac tcgaagcagt agatttaaga caattttac tgcataataa      9660 ctacgcatgg tgtcaagatc cctaaaaatt aacagaggca gacccagctc aagtattgac      9720
aaactcaagt ggcaactggc atatgaacaa ttttctcgtt caaatatatc tgaagcaatg      9780
tgtaaaacaa attagttttg ctccacacat ctgacaataa ttttttttcag taagcagact      9840 tactgtggat tcatatttgc gttgttgata gcgtttgata taatctgcct cgctagtcat      9900
gacgggagcg ttgccggtac c                                                9921
```

```
<210> SEQ ID NO 2
<211> LENGTH: 3972
<212> TYPE: DNA
<213> ORGANISM: Oryza officinalis
<220> FEATURE:
<221> NAME/KEY: CDS
<222> LOCATION: (1)..(3972)

<400> SEQUENCE: 2 atg gcg gag cta atg gcc acc atg gtg gtc ggg cca ctg ctg tcc atg      48
Met Ala Glu Leu Met Ala Thr Met Val Val Gly Pro Leu Leu Ser Met
1               5                   10                  15 gtg aag gac aag gcc tcc agc tac ctc ctg gag cag tac aag gtg atg      96
Val Lys Asp Lys Ala Ser Ser Tyr Leu Leu Glu Gln Tyr Lys Val Met
            20                  25                  30 gag ggc atg gag gag cag cac gag atc ctc aaa cgc aag ctg cca gcc     144
Glu Gly Met Glu Glu Gln His Glu Ile Leu Lys Arg Lys Leu Pro Ala
        35                  40                  45
```

| | | |
|---|---|---|
| atc ctc gac gtc atc gcc gac gcc gag gag cag gcg gct aaa cac agg<br>Ile Leu Asp Val Ile Ala Asp Ala Glu Glu Gln Ala Ala Lys His Arg<br>50                       55                   60 | | 192 |
| gaa ggg gtg aaa gca tgg ctc gag gcg ctc cgg aag gtg gcc tac cag<br>Glu Gly Val Lys Ala Trp Leu Glu Ala Leu Arg Lys Val Ala Tyr Gln<br>65                       70                   75                   80 | | 240 |
| gcc aat gac gtc ttc gac gag ttc aag tac gag gca ctc cgc cgc aag<br>Ala Asn Asp Val Phe Asp Glu Phe Lys Tyr Glu Ala Leu Arg Arg Lys<br>                   85                   90                   95 | | 288 |
| gcc aag ggg cac tac aag atg ctc agc agc atg gtt gta atc aag ctc<br>Ala Lys Gly His Tyr Lys Met Leu Ser Ser Met Val Val Ile Lys Leu<br>                100                  105                  110 | | 336 |
| att cct act cac aac cgt att ctg ttc agt tat agg atg ggc aac aag<br>Ile Pro Thr His Asn Arg Ile Leu Phe Ser Tyr Arg Met Gly Asn Lys<br>               115                   120                  125 | | 384 |
| ctc agg atg att ctg aat gcc att gaa gtt cta att gaa gag atg aat<br>Leu Arg Met Ile Leu Asn Ala Ile Glu Val Leu Ile Glu Glu Met Asn<br>130                      135                  140 | | 432 |
| gcc ttt agg ttt aaa ttc cga cca gag cca cca atg tcg tcc atg aaa<br>Ala Phe Arg Phe Lys Phe Arg Pro Glu Pro Pro Met Ser Ser Met Lys<br>145                      150                  155                  160 | | 480 |
| tgg agg aag aca gat tct aaa atc tcc gac ctt tct ttg gac att gcc<br>Trp Arg Lys Thr Asp Ser Lys Ile Ser Asp Leu Ser Leu Asp Ile Ala<br>                       165                  170                  175 | | 528 |
| aac aac tca aga aag gaa gat aaa cag gag att gtc agc aga ttg ctt<br>Asn Asn Ser Arg Lys Glu Asp Lys Gln Glu Ile Val Ser Arg Leu Leu<br>               180                   185                  190 | | 576 |
| gtt cca gcc agc gaa ggg gat ctc act gtt ctt ccc att gta gga atg<br>Val Pro Ala Ser Glu Gly Asp Leu Thr Val Leu Pro Ile Val Gly Met<br>               195                   200                  205 | | 624 |
| ggg ggg atg ggc aag acc acc tta gcg cag ctc att tac aat gac cct<br>Gly Gly Met Gly Lys Thr Thr Leu Ala Gln Leu Ile Tyr Asn Asp Pro<br>210                      215                  220 | | 672 |
| gac att cag aag cat ttc cag ttg ctg ctc tgg gtg tgt gtt tcc gac<br>Asp Ile Gln Lys His Phe Gln Leu Leu Leu Trp Val Cys Val Ser Asp<br>225                      230                  235                  240 | | 720 |
| aac ttc gat gtg gat ttg ctg gct aaa agc ata gtt gaa gca gct cgc<br>Asn Phe Asp Val Asp Leu Leu Ala Lys Ser Ile Val Glu Ala Ala Arg<br>                       245                  250                  255 | | 768 |
| aaa cag aag aat gat aac agt gga agt act aac aag tca cca ttg gat<br>Lys Gln Lys Asn Asp Asn Ser Gly Ser Thr Asn Lys Ser Pro Leu Asp<br>               260                   265                  270 | | 816 |
| gaa ctt aaa gaa gtt gtg agt ggg cag agg tac ctc ctc gtt ttg gat<br>Glu Leu Lys Glu Val Val Ser Gly Gln Arg Tyr Leu Leu Val Leu Asp<br>               275                   280                  285 | | 864 |
| gat gtc tgg aac cgt gat gct cgt aag tgg gaa gcg ctc aag tcc tac<br>Asp Val Trp Asn Arg Asp Ala Arg Lys Trp Glu Ala Leu Lys Ser Tyr<br>290                      295                  300 | | 912 |
| ctt cag cac ggt ggc agc ggt agc tca gtt ttg aca aca act cgt gat<br>Leu Gln His Gly Gly Ser Gly Ser Ser Val Leu Thr Thr Thr Arg Asp<br>305                      310                  315                  320 | | 960 |
| caa gaa gtg gct caa gtg atg gct cca gct caa aaa cct tat gat ctc<br>Gln Glu Val Ala Gln Val Met Ala Pro Ala Gln Lys Pro Tyr Asp Leu<br>                       325                  330                  335 | | 1008 |
| aag aga ctg aag gaa agc ttc ata gag gaa att atc agg aca agt gct<br>Lys Arg Leu Lys Glu Ser Phe Ile Glu Glu Ile Ile Arg Thr Ser Ala<br>               340                   345                  350 | | 1056 |
| ttc agt tca caa caa gaa agg cct cct gag ctt ctc aaa atg gtt ggt<br>Phe Ser Ser Gln Gln Glu Arg Pro Pro Glu Leu Leu Lys Met Val Gly<br>               355                   360                  365 | | 1104 |

-continued

| | |
|---|---|
| gat att gcc aag aaa tgt tct ggt tcc cct tta gct gca aca gca ttg<br>Asp Ile Ala Lys Lys Cys Ser Gly Ser Pro Leu Ala Ala Thr Ala Leu<br>370 375 380 | 1152 |
| ggc tct aca ctg cgt acg aag acc acc aag aaa gaa tgg gag gct ata<br>Gly Ser Thr Leu Arg Thr Lys Thr Thr Lys Lys Glu Trp Glu Ala Ile<br>385 390 395 400 | 1200 |
| tta agc aga agc aca att tgc gat gag gaa aat gga att tta cca ata<br>Leu Ser Arg Ser Thr Ile Cys Asp Glu Glu Asn Gly Ile Leu Pro Ile<br>405 410 415 | 1248 |
| ctc aag ctc agt tac aat tgc ttg cca tca tat atg cgg caa tgc ttt<br>Leu Lys Leu Ser Tyr Asn Cys Leu Pro Ser Tyr Met Arg Gln Cys Phe<br>420 425 430 | 1296 |
| tcc ttt tgt gca att ttc ccc aag gat cat gag att gac gtg gaa atg<br>Ser Phe Cys Ala Ile Phe Pro Lys Asp His Glu Ile Asp Val Glu Met<br>435 440 445 | 1344 |
| ctg atc cag tta tgg atg gcc aat ggt ttt atc cca gag caa caa gga<br>Leu Ile Gln Leu Trp Met Ala Asn Gly Phe Ile Pro Glu Gln Gln Gly<br>450 455 460 | 1392 |
| gag tgc cct gaa atc att ggt aaa aga att ttc agt gag ttg gtg tca<br>Glu Cys Pro Glu Ile Ile Gly Lys Arg Ile Phe Ser Glu Leu Val Ser<br>465 470 475 480 | 1440 |
| agg tca ttt ttt cag gat gcg aaa ggg atc ccg ttt gag ttc cat gat<br>Arg Ser Phe Phe Gln Asp Ala Lys Gly Ile Pro Phe Glu Phe His Asp<br>485 490 495 | 1488 |
| ata aag aac tct aag att act tgt aag atc cat gac ctt atg cat gat<br>Ile Lys Asn Ser Lys Ile Thr Cys Lys Ile His Asp Leu Met His Asp<br>500 505 510 | 1536 |
| gtt gca caa tcc tcc atg gga aaa gaa tgc gct gct ata gat aca gaa<br>Val Ala Gln Ser Ser Met Gly Lys Glu Cys Ala Ala Ile Asp Thr Glu<br>515 520 525 | 1584 |
| gtt agt aaa agt gag gat ttt cct tat tct gct cgc cat cta ttt ttg<br>Val Ser Lys Ser Glu Asp Phe Pro Tyr Ser Ala Arg His Leu Phe Leu<br>530 535 540 | 1632 |
| tca ggt gat aga cca gaa gct att cgg act cct tcc cca gag aaa gga<br>Ser Gly Asp Arg Pro Glu Ala Ile Arg Thr Pro Ser Pro Glu Lys Gly<br>545 550 555 560 | 1680 |
| tat cca ggt atc caa aca tta ata tgt tca cgt ttc aaa tat ttg cag<br>Tyr Pro Gly Ile Gln Thr Leu Ile Cys Ser Arg Phe Lys Tyr Leu Gln<br>565 570 575 | 1728 |
| aat gta tca aaa tac agg tca ttg cga gta tta aca acg atg tgg gaa<br>Asn Val Ser Lys Tyr Arg Ser Leu Arg Val Leu Thr Thr Met Trp Glu<br>580 585 590 | 1776 |
| ggt tca ttc ctg ata cca aaa tat cat cat cac ctg agg tat ctt gat<br>Gly Ser Phe Leu Ile Pro Lys Tyr His His His Leu Arg Tyr Leu Asp<br>595 600 605 | 1824 |
| ctc tca gaa agt gaa att aaa gca ctt cct gaa gac ata agc atc cta<br>Leu Ser Glu Ser Glu Ile Lys Ala Leu Pro Glu Asp Ile Ser Ile Leu<br>610 615 620 | 1872 |
| tat cat ttg caa aca ttg aac ctt tcc cgt tgt tta tct ctc cgt cga<br>Tyr His Leu Gln Thr Leu Asn Leu Ser Arg Cys Leu Ser Leu Arg Arg<br>625 630 635 640 | 1920 |
| ctt cca aag gga atg aag tac atg acc gcc ctc cgt cac ttg tac act<br>Leu Pro Lys Gly Met Lys Tyr Met Thr Ala Leu Arg His Leu Tyr Thr<br>645 650 655 | 1968 |
| cac gga tgt tgg agt tta gga agc atg cct cct gac ctc gga cac ctc<br>His Gly Cys Trp Ser Leu Gly Ser Met Pro Pro Asp Leu Gly His Leu<br>660 665 670 | 2016 |
| act tgc cta cag acg ctt aca tgc ttt gta gcc ggt act tgc tct ggc<br>Thr Cys Leu Gln Thr Leu Thr Cys Phe Val Ala Gly Thr Cys Ser Gly | 2064 |

-continued

```
                 675                 680                 685
tgc agt gat ttg gga gag ctg cgg cag ttg gac ctt ggt ggt cga cta       2112
Cys Ser Asp Leu Gly Glu Leu Arg Gln Leu Asp Leu Gly Gly Arg Leu
    690                 695                 700 gag cta aga aaa ctg gaa aat gtg aca aaa gct gat gca aaa gca gca       2160
Glu Leu Arg Lys Leu Glu Asn Val Thr Lys Ala Asp Ala Lys Ala Ala
705                 710                 715                 720 aat ctc gga aag aag gaa aaa ctg acc aaa ttg acc tta ata tgg act       2208
Asn Leu Gly Lys Lys Glu Lys Leu Thr Lys Leu Thr Leu Ile Trp Thr
                725                 730                 735 gat cag gag tac aag gag gca cag agt aat aat cat aaa gag gtg ctg       2256
Asp Gln Glu Tyr Lys Glu Ala Gln Ser Asn Asn His Lys Glu Val Leu
        740                 745                 750 gaa ggt ctc acg cct cac gag ggg ctc aag gtt ctg agt ata tat cac       2304
Glu Gly Leu Thr Pro His Glu Gly Leu Lys Val Leu Ser Ile Tyr His
            755                 760                 765 tgt ggg agc agt aca tgt cca act tgg atg aat aaa ctg cgg gac atg       2352
Cys Gly Ser Ser Thr Cys Pro Thr Trp Met Asn Lys Leu Arg Asp Met
770                 775                 780 gtg ggg ctt gag tta aat ggt tgc aaa aat ctc gag aag ctt cct ccg       2400
Val Gly Leu Glu Leu Asn Gly Cys Lys Asn Leu Glu Lys Leu Pro Pro
785                 790                 795                 800 ttg tgg cag cta ccg gct cta caa gtt ctt tgc ctg gaa gga ctg ggt       2448
Leu Trp Gln Leu Pro Ala Leu Gln Val Leu Cys Leu Glu Gly Leu Gly
                805                 810                 815 agt tta aat tgc ttg ttc aac tgt gac aca cac acc ccc ttc aca ttt       2496
Ser Leu Asn Cys Leu Phe Asn Cys Asp Thr His Thr Pro Phe Thr Phe
        820                 825                 830 tgc aga ctg aag gag cta acc ttg tct gat atg aca aat ttt gag aca       2544
Cys Arg Leu Lys Glu Leu Thr Leu Ser Asp Met Thr Asn Phe Glu Thr
            835                 840                 845 tgg tgg gac aca aat gag gta caa gga gaa gag ctg atg ttt cct gag       2592
Trp Trp Asp Thr Asn Glu Val Gln Gly Glu Glu Leu Met Phe Pro Glu
850                 855                 860 gtt gaa aag ctg tca atc gaa agt tgc cat agg cta act gcc ttg cca       2640
Val Glu Lys Leu Ser Ile Glu Ser Cys His Arg Leu Thr Ala Leu Pro
865                 870                 875                 880 aaa gca tca aat gcg att tca gaa tcg tcc ggc gaa gtt agc acc gtg       2688
Lys Ala Ser Asn Ala Ile Ser Glu Ser Ser Gly Glu Val Ser Thr Val
                885                 890                 895 tgt cgt tct gca ttt cca gca ttg aag gaa atg aaa tta tat gat ttg       2736
Cys Arg Ser Ala Phe Pro Ala Leu Lys Glu Met Lys Leu Tyr Asp Leu
        900                 905                 910 cgt atc ttt cag aaa tgg gag gca gtc gat gga act cca agg gag gag       2784
Arg Ile Phe Gln Lys Trp Glu Ala Val Asp Gly Thr Pro Arg Glu Glu
            915                 920                 925 gca aca ttt cct cag ctt gac aaa tta gaa atc aga cag tgc cca gag       2832
Ala Thr Phe Pro Gln Leu Asp Lys Leu Glu Ile Arg Gln Cys Pro Glu
930                 935                 940 ctg act act cta cct gaa gca cca aag cta agt gac tta gag ata tct       2880
Leu Thr Thr Leu Pro Glu Ala Pro Lys Leu Ser Asp Leu Glu Ile Ser
945                 950                 955                 960 aaa ggc aat caa caa ata tcc cta cag gca gcc agc aga cat att act       2928
Lys Gly Asn Gln Gln Ile Ser Leu Gln Ala Ala Ser Arg His Ile Thr
                965                 970                 975 tca ttg tcc agt ctc gtt ctg cat ttg tcc act gat gac aca gaa aca       2976
Ser Leu Ser Ser Leu Val Leu His Leu Ser Thr Asp Asp Thr Glu Thr
        980                 985                 990 gca tcg gtg gcc aag caa caa gat  tcg agt gat ttg gtg  att gag gat    3024
```

-continued

```
            Ala Ser Val Ala Lys Gln Gln Asp  Ser Ser Asp Leu Val  Ile Glu Asp
                      995               1000              1005 gag aaa tgg agt cat aaa tct ccc ctg gaa ctt atg gtc ttg agt         3069
Glu Lys Trp Ser His Lys Ser Pro Leu Glu Leu Met Val Leu Ser
1010                1015                1020 cgg tgc aac ctt tta ttc tct cac cca agt gca ctg gct ctg tgg         3114
Arg Cys Asn Leu Leu Phe Ser His Pro Ser Ala Leu Ala Leu Trp
1025                1030                1035 aca tgt ttt gct cag ctc cta gat ctg aaa att cgg tat gtt gat         3159
Thr Cys Phe Ala Gln Leu Leu Asp Leu Lys Ile Arg Tyr Val Asp
1040                1045                1050 gcg ctt gtc agc tgg cca gaa gag gtg ttc cag ggc tta gtt tcc         3204
Ala Leu Val Ser Trp Pro Glu Glu Val Phe Gln Gly Leu Val Ser
1055                1060                1065 ttg agg aag tta gag att tct gta tgc gag aat ctg aca gga cac         3249
Leu Arg Lys Leu Glu Ile Ser Val Cys Glu Asn Leu Thr Gly His
1070                1075                1080 aca caa gct cgt ggg caa tct aca ccc gca cca agt gaa ctc ctg         3294
Thr Gln Ala Arg Gly Gln Ser Thr Pro Ala Pro Ser Glu Leu Leu
1085                1090                1095 cca cgt ttg gag tcc cta gag ata acg tgt tgt gat tct att gtg         3339
Pro Arg Leu Glu Ser Leu Glu Ile Thr Cys Cys Asp Ser Ile Val
1100                1105                1110 gag gtc ccc aat cta ccg gcg tct ctc aag cta tta gaa att agg         3384
Glu Val Pro Asn Leu Pro Ala Ser Leu Lys Leu Leu Glu Ile Arg
1115                1120                1125 ggg tgc ccc ggc ctg gag tcc atc gta ttc aat cag cag cag gat         3429
Gly Cys Pro Gly Leu Glu Ser Ile Val Phe Asn Gln Gln Gln Asp
1130                1135                1140 agg acg atg ttg gtg agt gca gaa agc ttt gca gag cag gat aag         3474
Arg Thr Met Leu Val Ser Ala Glu Ser Phe Ala Glu Gln Asp Lys
1145                1150                1155 tca tcg tta ata tca ggg tcc aca agc gag acc aac gat cac gtc         3519
Ser Ser Leu Ile Ser Gly Ser Thr Ser Glu Thr Asn Asp His Val
1160                1165                1170 ctt cca cgc cta gaa tct ctt gta ata aat tgg tgc gat cgt ttg         3564
Leu Pro Arg Leu Glu Ser Leu Val Ile Asn Trp Cys Asp Arg Leu
1175                1180                1185 gag gtt ctc cat ctt cct ccg tcc atc aag aaa ttg ggt att tat         3609
Glu Val Leu His Leu Pro Pro Ser Ile Lys Lys Leu Gly Ile Tyr
1190                1195                1200 agc tgt gaa aaa ctt cgg tcc ctc tca gta aag ctg gat gcc gtt         3654
Ser Cys Glu Lys Leu Arg Ser Leu Ser Val Lys Leu Asp Ala Val
1205                1210                1215 cga gaa tta agt atc aga cat tgc ggg agc ttg aaa tca ctg gaa         3699
Arg Glu Leu Ser Ile Arg His Cys Gly Ser Leu Lys Ser Leu Glu
1220                1225                1230 tct tgc tta gga gag ctc gcg tcg ctg caa caa ctc aaa ctt ttt         3744
Ser Cys Leu Gly Glu Leu Ala Ser Leu Gln Gln Leu Lys Leu Phe
1235                1240                1245 gat tgc aag agc ctg gaa tcc ttg ccg aag ggg cct caa gca tac         3789
Asp Cys Lys Ser Leu Glu Ser Leu Pro Lys Gly Pro Gln Ala Tyr
1250                1255                1260 tca tct ctt aca tct ctt gaa att cgt ggt tgt tct ggt ata aag         3834
Ser Ser Leu Thr Ser Leu Glu Ile Arg Gly Cys Ser Gly Ile Lys
1265                1270                1275 gtg ctt cca ccg agc cta cag caa cgt ctg gat gac atc gag gac         3879
Val Leu Pro Pro Ser Leu Gln Gln Arg Leu Asp Asp Ile Glu Asp
1280                1285                1290
```

-continued

| | |
|---|---|
| aaa gaa cta gat gcc tgc tat gaa gag gca gaa gca gaa cca aag<br>Lys Glu Leu Asp Ala Cys Tyr Glu Glu Ala Glu Ala Glu Pro Lys<br>1295                           1300                       1305 | 3924 |
| tct cgt cat cgt caa tct gca atc agt agg ctg atg tgc ttg aag<br>Ser Arg His Arg Gln Ser Ala Ile Ser Arg Leu Met Cys Leu Lys<br>1310                           1315                       1320 | 3969 |
| tag | 3972 |

<210> SEQ ID NO 3
<211> LENGTH: 1323
<212> TYPE: PRT
<213> ORGANISM: Oryza officinalis

<400> SEQUENCE: 3

Met Ala Glu Leu Met Ala Thr Met Val Val Gly Pro Leu Leu Ser Met
1                 5                   10                  15

Val Lys Asp Lys Ala Ser Ser Tyr Leu Leu Glu Gln Tyr Lys Val Met
                  20                   25                   30

Glu Gly Met Glu Glu Gln His Glu Ile Leu Lys Arg Lys Leu Pro Ala
         35                     40                   45

Ile Leu Asp Val Ile Ala Asp Ala Glu Glu Ala Ala Lys His Arg
    50                   55                   60

Glu Gly Val Lys Ala Trp Leu Glu Ala Leu Arg Lys Val Ala Tyr Gln
65                70                   75                   80

Ala Asn Asp Val Phe Asp Glu Phe Lys Tyr Glu Ala Leu Arg Arg Lys
                  85                   90                   95

Ala Lys Gly His Tyr Lys Met Leu Ser Ser Met Val Val Ile Lys Leu
         100                    105                 110

Ile Pro Thr His Asn Arg Ile Leu Phe Ser Tyr Arg Met Gly Asn Lys
        115                    120                 125

Leu Arg Met Ile Leu Asn Ala Ile Glu Val Leu Ile Glu Glu Met Asn
130               135                   140

Ala Phe Arg Phe Lys Phe Arg Pro Glu Pro Met Ser Ser Met Lys
145               150                   155                   160

Trp Arg Lys Thr Asp Ser Lys Ile Ser Asp Leu Ser Leu Asp Ile Ala
               165                   170                 175

Asn Asn Ser Arg Lys Glu Asp Lys Gln Glu Ile Val Ser Arg Leu Leu
         180                    185                 190

Val Pro Ala Ser Glu Gly Asp Leu Thr Val Leu Pro Ile Val Gly Met
        195                    200                 205

Gly Gly Met Gly Lys Thr Thr Leu Ala Gln Leu Ile Tyr Asn Asp Pro
210               215                   220

Asp Ile Gln Lys His Phe Gln Leu Leu Leu Trp Val Cys Val Ser Asp
225               230                   235                   240

Asn Phe Asp Val Asp Leu Leu Ala Lys Ser Ile Val Glu Ala Ala Arg
               245                   250                 255

Lys Gln Lys Asn Asp Asn Ser Gly Ser Thr Asn Lys Ser Pro Leu Asp
         260                    265                 270

Glu Leu Lys Glu Val Val Ser Gly Gln Arg Tyr Leu Leu Val Leu Asp
        275                    280                 285

Asp Val Trp Asn Arg Asp Ala Arg Lys Trp Glu Ala Leu Lys Ser Tyr
        290                    295                 300

Leu Gln His Gly Gly Ser Gly Ser Ser Val Leu Thr Thr Thr Arg Asp
305               310                   315                   320

Gln Glu Val Ala Gln Val Met Ala Pro Ala Gln Lys Pro Tyr Asp Leu

-continued

```
                325                 330                 335
Lys Arg Leu Lys Glu Ser Phe Ile Glu Glu Ile Ile Arg Thr Ser Ala
                340                 345                 350
Phe Ser Ser Gln Gln Glu Arg Pro Pro Glu Leu Leu Lys Met Val Gly
                355                 360                 365
Asp Ile Ala Lys Lys Cys Ser Gly Ser Pro Leu Ala Ala Thr Ala Leu
370                 375                 380
Gly Ser Thr Leu Arg Thr Lys Thr Thr Lys Lys Glu Trp Glu Ala Ile
385                 390                 395                 400
Leu Ser Arg Ser Thr Ile Cys Asp Glu Glu Asn Gly Ile Leu Pro Ile
                405                 410                 415
Leu Lys Leu Ser Tyr Asn Cys Leu Pro Ser Tyr Met Arg Gln Cys Phe
                420                 425                 430
Ser Phe Cys Ala Ile Phe Pro Lys Asp His Glu Ile Asp Val Glu Met
                435                 440                 445
Leu Ile Gln Leu Trp Met Ala Asn Gly Phe Ile Pro Glu Gln Gln Gly
                450                 455                 460
Glu Cys Pro Glu Ile Ile Gly Lys Arg Ile Phe Ser Glu Leu Val Ser
465                 470                 475                 480
Arg Ser Phe Phe Gln Asp Ala Lys Gly Ile Pro Phe Glu Phe His Asp
                485                 490                 495
Ile Lys Asn Ser Lys Ile Thr Cys Lys Ile His Asp Leu Met His Asp
                500                 505                 510
Val Ala Gln Ser Ser Met Gly Lys Glu Cys Ala Ala Ile Asp Thr Glu
                515                 520                 525
Val Ser Lys Ser Glu Asp Phe Pro Tyr Ser Ala Arg His Leu Phe Leu
                530                 535                 540
Ser Gly Asp Arg Pro Glu Ala Ile Arg Thr Pro Ser Pro Glu Lys Gly
545                 550                 555                 560
Tyr Pro Gly Ile Gln Thr Leu Ile Cys Ser Arg Phe Lys Tyr Leu Gln
                565                 570                 575
Asn Val Ser Lys Tyr Arg Ser Leu Arg Val Leu Thr Thr Met Trp Glu
                580                 585                 590
Gly Ser Phe Leu Ile Pro Lys Tyr His His Leu Arg Tyr Leu Asp
                595                 600                 605
Leu Ser Glu Ser Glu Ile Lys Ala Leu Pro Glu Asp Ile Ser Ile Leu
                610                 615                 620
Tyr His Leu Gln Thr Leu Asn Leu Ser Arg Cys Leu Ser Leu Arg Arg
625                 630                 635                 640
Leu Pro Lys Gly Met Lys Tyr Met Thr Ala Leu Arg His Leu Tyr Thr
                645                 650                 655
His Gly Cys Trp Ser Leu Gly Ser Met Pro Pro Asp Leu Gly His Leu
                660                 665                 670
Thr Cys Leu Gln Thr Leu Thr Cys Phe Val Ala Gly Thr Cys Ser Gly
                675                 680                 685
Cys Ser Asp Leu Gly Glu Leu Arg Gln Leu Asp Leu Gly Gly Arg Leu
                690                 695                 700
Glu Leu Arg Lys Leu Glu Asn Val Thr Lys Ala Asp Ala Lys Ala Ala
705                 710                 715                 720
Asn Leu Gly Lys Lys Glu Lys Leu Thr Lys Leu Thr Leu Ile Trp Thr
                725                 730                 735
Asp Gln Glu Tyr Lys Glu Ala Gln Ser Asn Asn His Lys Glu Val Leu
                740                 745                 750
```

-continued

Glu Gly Leu Thr Pro His Glu Gly Leu Lys Val Leu Ser Ile Tyr His
          755                 760                 765

Cys Gly Ser Ser Thr Cys Pro Thr Trp Met Asn Lys Leu Arg Asp Met
    770                 775                 780

Val Gly Leu Glu Leu Asn Gly Cys Lys Asn Leu Glu Lys Leu Pro Pro
785                 790                 795                 800

Leu Trp Gln Leu Pro Ala Leu Gln Val Leu Cys Leu Glu Gly Leu Gly
                805                 810                 815

Ser Leu Asn Cys Leu Phe Asn Cys Asp Thr His Thr Pro Phe Thr Phe
            820                 825                 830

Cys Arg Leu Lys Glu Leu Thr Leu Ser Asp Met Thr Asn Phe Glu Thr
                835                 840                 845

Trp Trp Asp Thr Asn Glu Val Gln Gly Glu Glu Leu Met Phe Pro Glu
    850                 855                 860

Val Glu Lys Leu Ser Ile Glu Ser Cys His Arg Leu Thr Ala Leu Pro
865                 870                 875                 880

Lys Ala Ser Asn Ala Ile Ser Glu Ser Ser Gly Glu Val Ser Thr Val
                885                 890                 895

Cys Arg Ser Ala Phe Pro Ala Leu Lys Glu Met Lys Leu Tyr Asp Leu
                900                 905                 910

Arg Ile Phe Gln Lys Trp Glu Ala Val Asp Gly Thr Pro Arg Glu Glu
                915                 920                 925

Ala Thr Phe Pro Gln Leu Asp Lys Leu Glu Ile Arg Gln Cys Pro Glu
    930                 935                 940

Leu Thr Thr Leu Pro Glu Ala Pro Lys Leu Ser Asp Leu Glu Ile Ser
945                 950                 955                 960

Lys Gly Asn Gln Gln Ile Ser Leu Gln Ala Ala Ser Arg His Ile Thr
                965                 970                 975

Ser Leu Ser Ser Leu Val Leu His Leu Ser Thr Asp Asp Thr Glu Thr
            980                 985                 990

Ala Ser Val Ala Lys Gln Gln Asp Ser Ser Asp Leu Val Ile Glu Asp
        995                 1000                1005

Glu Lys Trp Ser His Lys Ser Pro Leu Glu Leu Met Val Leu Ser
    1010                1015                1020

Arg Cys Asn Leu Leu Phe Ser His Pro Ser Ala Leu Ala Leu Trp
    1025                1030                1035

Thr Cys Phe Ala Gln Leu Leu Asp Leu Lys Ile Arg Tyr Val Asp
    1040                1045                1050

Ala Leu Val Ser Trp Pro Glu Glu Val Phe Gln Gly Leu Val Ser
    1055                1060                1065

Leu Arg Lys Leu Glu Ile Ser Val Cys Glu Asn Leu Thr Gly His
    1070                1075                1080

Thr Gln Ala Arg Gly Gln Ser Thr Pro Ala Pro Ser Glu Leu Leu
    1085                1090                1095

Pro Arg Leu Glu Ser Leu Glu Ile Thr Cys Cys Asp Ser Ile Val
    1100                1105                1110

Glu Val Pro Asn Leu Pro Ala Ser Leu Lys Leu Leu Glu Ile Arg
    1115                1120                1125

Gly Cys Pro Gly Leu Glu Ser Ile Val Phe Asn Gln Gln Gln Asp
    1130                1135                1140

Arg Thr Met Leu Val Ser Ala Glu Ser Phe Ala Glu Gln Asp Lys
    1145                1150                1155

Ser Ser Leu Ile Ser Gly Ser Thr Ser Glu Thr Asn Asp His Val
1160             1165             1170

Leu Pro Arg Leu Glu Ser Leu Val Ile Asn Trp Cys Asp Arg Leu
1175             1180             1185

Glu Val Leu His Leu Pro Pro Ser Ile Lys Lys Leu Gly Ile Tyr
1190             1195             1200

Ser Cys Glu Lys Leu Arg Ser Leu Ser Val Lys Leu Asp Ala Val
1205             1210             1215

Arg Glu Leu Ser Ile Arg His Cys Gly Ser Leu Lys Ser Leu Glu
1220             1225             1230

Ser Cys Leu Gly Glu Leu Ala Ser Leu Gln Gln Leu Lys Leu Phe
1235             1240             1245

Asp Cys Lys Ser Leu Glu Ser Leu Pro Lys Gly Pro Gln Ala Tyr
1250             1255             1260

Ser Ser Leu Thr Ser Leu Glu Ile Arg Gly Cys Ser Gly Ile Lys
1265             1270             1275

Val Leu Pro Pro Ser Leu Gln Gln Arg Leu Asp Asp Ile Glu Asp
1280             1285             1290

Lys Glu Leu Asp Ala Cys Tyr Glu Glu Ala Glu Ala Glu Pro Lys
1295             1300             1305

Ser Arg His Arg Gln Ser Ala Ile Ser Arg Leu Met Cys Leu Lys
1310             1315             1320

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ctccctgact gaagaagaga agag                                    24

<210> SEQ ID NO 5
<211> LENGTH: 25
<212> TYPE: DNA
<213> ORGANISM: Artificial Sequence
<220> FEATURE:
<223> OTHER INFORMATION: primer

<400> SEQUENCE: 5
tgctagctgt gattctctta tgatg                                   25

<210> SEQ ID NO 6
<211> LENGTH: 32
<212> TYPE: DNA
<213> ORGANISM: Artificial Sequence
<220> FEATURE:
<223> OTHER INFORMATION: primer

<400> SEQUENCE: 6
cggaattcct ccctgactga agaagagaag ag                           32

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
cggaattctg ctagctgtga ttctcttatg atg    33

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
tcccccgggg atggcggagc taatggccac    30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
gctctagact acttcaagca catcagccta    30

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
cggaattcat ggtggagcac gacactct    28

<210> SEQ ID NO 11
<211> LENGTH: 30
<212> TYPE: DNA
<213> ORGANISM: Artificial Sequence
<220> FEATURE:
<223> OTHER INFORMATION: primer

<400> SEQUENCE: 11
tcccccgggg atctcattgc ccccgggat    30

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ctgctgctgc tctcgtattg    20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cagggaagct ccaagaacag    20

<210> SEQ ID NO 14
<211> LENGTH: 20
<212> TYPE: DNA
<213> ORGANISM: Artificial Sequence

```
<220> FEATURE:
<223> OTHER INFORMATION: primer

<400> SEQUENCE: 14
tccacctttg caaatccaat                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cttcttcctc tggctggcta                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ccggcgagaa gttctacctc                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gctgtaatcc tgcgtgtcct                                               20

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
tgtgggtttt gcttctcact t                                             21

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
caaaccactg tgagtacggc ta                                            22

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
agaaatggtg aaagatggtg ctaccg                                        26
```

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
ctgaatgttc ttcaactccc agtgc                                         25

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
agcgttaagc gccattatca                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cgccgaggca ttagagtaga                                               20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctgctgctgc tctcgtattg                                               20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cagggaagct ccaagaacag                                               20

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gcaaatatgt gcatacctgg a                                             21

```
<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
ctgacatctc cgcctgga                                                18
```